(12) United States Patent
Brown, Jr. et al.

(10) Patent No.: US 7,740,657 B2
(45) Date of Patent: Jun. 22, 2010

(54) SOFT TISSUE SOCK ENHANCEMENT DEVICES

(76) Inventors: Charles H. Brown, Jr., 15 Cedar St., Wellesley, MA (US) 02181; Bernard J. Bourque, 17 Fremont St., Taunton, MA (US) 02780; Rebecca A. Blough, 40 Crossing Dr., Apt. 103, Cumberland, RI (US) 02864; Michael C. Ferragamo, 2355 Old Wellington St., Dighton, MA (US) 02715; Raymond A. Bojarski, 32 Colleens Way, Attleboro, MA (US) 02703; Paul Alexander Torrie, 8 Bowden St., Marblehead, CA (US) 01945; Ben K. Graf, 135 N. Prospect St., Madison, WI (US) 53701; Fraser Harvie, 33 Loch Striven, St. Leonards, East Kilbride (GB); Steve Ek, 49 Powder Hill Rd., Bolton, MA (US) 01740

( * ) Notice: Subject to any disclaimer, the term of this patent is extended or adjusted under 35 U.S.C. 154(b) by 267 days.

(21) Appl. No.: 11/866,917

(22) Filed: Oct. 3, 2007

(65) Prior Publication Data

US 2008/0027445 A1    Jan. 31, 2008

Related U.S. Application Data

(63) Continuation of application No. 10/357,500, filed on Feb. 4, 2003, now Pat. No. 7,279,008, which is a continuation-in-part of application No. 09/526,960, filed on Mar. 16, 2000, now Pat. No. 6,746,483.

(51) Int. Cl.
*A61F 2/08* (2006.01)

(52) U.S. Cl. .................................. 623/13.15; 623/13.14

(58) Field of Classification Search .... 623/13.11–13.19
See application file for complete search history.

(56) References Cited

U.S. PATENT DOCUMENTS 3,921,496 A    11/1975    Helderman (Continued)

FOREIGN PATENT DOCUMENTS

EP    0 280 572 A1    8/1988

(Continued)

OTHER PUBLICATIONS

USPTO Non-Final Office Acton in U.S. Appl. No. 11/970,196, mailed May 6, 2009, 8 pages.

(Continued)

*Primary Examiner*—David H Willse
*Assistant Examiner*—Javier G Blanco
(74) *Attorney, Agent, or Firm*—Norman F. Hainer, Jr.

(57) ABSTRACT

A sheath for organizing soft tissue includes a first tube having a flexible body sized and shaped to receive a fixation device, and a second tube coupled to the first tube having a flexible body sized and shaped to receive a soft tissue graft. A method for implanting soft tissue in a bone tunnel includes coupling a soft tissue graft to a sheath assembly; and positioning the sheath assembly relative to the soft tissue graft based on a measured depth of a bone tunnel. A set of surgical devices for implanting soft tissue grafts in a bone tunnel includes a sheath assembly, a measurement device for measuring the depth of the bone tunnel, a securing element configured to secure the sheath assembly to the soft tissue graft at a position determined by the measured bone tunnel depth, and a tensioning device configured to organize a plurality of soft tissue grafts.

12 Claims, 27 Drawing Sheets

U.S. PATENT DOCUMENTS

| | | | |
|---|---|---|---|
| 4,469,101 A | 9/1984 | Coleman et al. | |
| 4,605,414 A | 8/1986 | Czajka | |
| 4,790,850 A | 12/1988 | Dunn et al. | |
| 5,071,420 A | 12/1991 | Paulos et al. | |
| 5,084,050 A | 1/1992 | Draenert | |
| 5,139,520 A | 8/1992 | Rosenberg | |
| 5,197,976 A | 3/1993 | Herweck et al. | |
| 5,383,878 A | 1/1995 | Roger et al. | |
| 5,439,684 A | 8/1995 | Prewett et al. | |
| 5,456,274 A | 10/1995 | Selbee et al. | |
| 5,456,721 A | 10/1995 | Legrand | |
| 5,490,750 A | 2/1996 | Gundy | |
| 5,632,748 A | 5/1997 | Beck, Jr. et al. | |
| 5,641,256 A | 6/1997 | Gundy | |
| 5,671,695 A | 9/1997 | Schroeder | |
| 5,683,419 A | 11/1997 | Thal | |
| 5,713,904 A | 2/1998 | Errico et al. | |
| 5,716,359 A | 2/1998 | Ojima et al. | |
| 5,720,765 A | 2/1998 | Thal | |
| 5,769,894 A | 6/1998 | Ferragamo | |
| 5,899,938 A | 5/1999 | Sklar et al. | |
| 5,935,129 A | 8/1999 | McDevitt et al. | |
| 5,964,764 A | 10/1999 | West et al. | |
| 5,984,926 A | 11/1999 | Jones | |
| 6,203,572 B1 | 3/2001 | Johnson | |
| 6,409,750 B1 | 6/2002 | Hyodoh et al. | |
| 6,454,808 B1 | 9/2002 | Masada | |
| 6,533,816 B2 | 3/2003 | Sklar | |
| 6,602,290 B2 | 8/2003 | Esnouf et al. | |
| 6,840,770 B2 | 1/2005 | McDevitt | |
| 7,220,283 B2 | 5/2007 | Terrill | |
| 7,279,008 B2 | 10/2007 | Brown et al. | |
| 7,407,512 B2 | 8/2008 | Bojarski et al. | |
| 2002/0055749 A1 | 5/2002 | Esnouf et al. | |
| 2002/0108622 A1 | 8/2002 | Whelan | |
| 2009/0202963 A1 | 8/2009 | McDevitt | |

FOREIGN PATENT DOCUMENTS

| | | |
|---|---|---|
| EP | 0 556 571 A1 | 8/1993 |
| EP | 0 893 109 | 1/1999 |
| FR | 2714817 | 7/1995 |
| JP | 10014936 A | 1/1998 |
| WO | 98/22047 | 5/1998 |
| WO | 98/37835 | 9/1998 |
| WO | 99/01084 | 1/1999 |
| WO | 01/70135 | 9/2001 |

OTHER PUBLICATIONS

Pinczewski et al., "Case Report—Integration of Hamstring Tendon Graft With Bone in Reconstruction of the Anterior Cruciate Ligament," Arthroscopy: The Journal of Arthroscopic and Related Surgery, vol. 13, No. 5, pp. 641-643 (Oct. 1997).

Innovasive Devices Website, BioROC EZ Bioabsorbable Suture Fastener, http://www.orthoindustry.com/biorocez.htm (no date).

Innovasive Devices Product Brochure, Intrafix ACL Tibial Fastener (no date).

Notification of Transmittal of the International Preliminary Report on Patentability mailed Jul. 27, 2005 for International Application No. PCT/US2004/003302 filed Feb. 4, 2004.

Partial International Search Report mailed Aug. 2, 2004, in PCT/US2004/003302.

International Search Report Form PCT/ISA/220 (10 pages).

International Search Report, PCT/US01/08124, mailed Oct. 29, 2001.

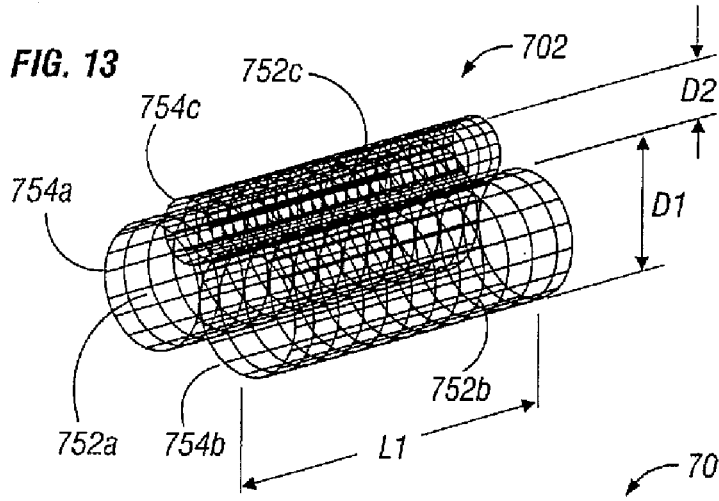
FIG. 13
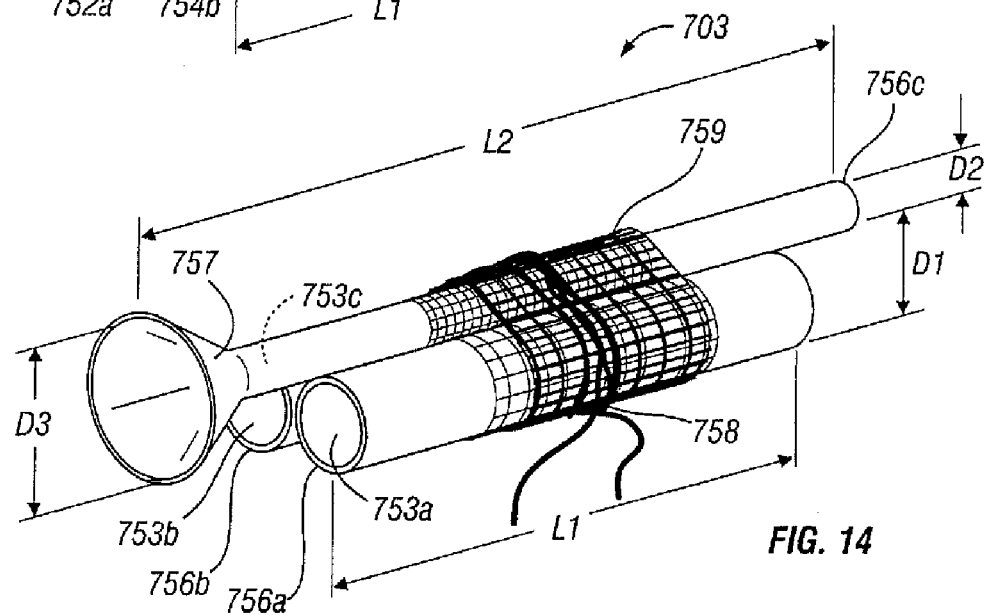
FIG. 14
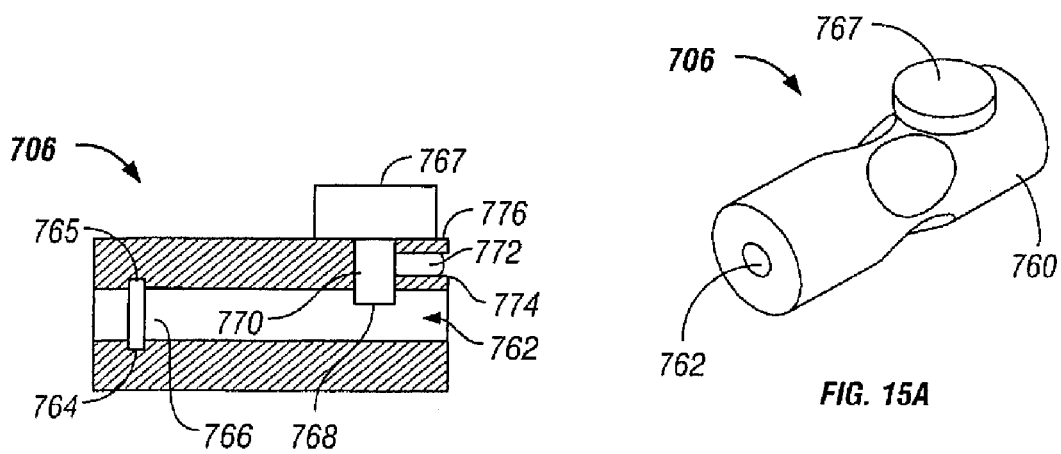
FIG. 15B
FIG. 15A

SOFT TISSUE SOCK ENHANCEMENT DEVICES

CROSS REFERENCE TO RELATED APPLICATIONS

This application is a continuation of application U.S. Ser. No. 10/357,500, filed Feb. 4, 2003, to be issued as U.S. Pat. No. 7,279,008, which is a continuation-in-part of application U.S. Ser. No. 09/526,960, titled "SHEATHS FOR IMPLANTABLE FIXATION DEVICES," filed Mar. 16, 2000, now U.S. Pat. No. 6,746,483.

BACKGROUND

The invention relates to devices that fix soft tissue to support structures, particularly devices that fix soft tissue grafts within bone tunnels.

In certain types of surgical procedures, soft tissue grafts must be fixed within a bone tunnel. For example, in anterior cruciate ligament (ACL) replacement surgery, a ligament graft is harvested from the patient or from a donor, and implanted within the knee by securing one end within a bone tunnel drilled through the tibia, and the other end within a bone tunnel drilled through the femur. Several ACL reconstructive techniques are described in Rosenberg, U.S. Pat. No. 5,139,520, which is incorporated herein by reference.

Referring to FIG. 1, a ligament graft 10 can be fixed within a bone tunnel using a bone screw 12. Graft 10 is made from e.g., a single or double long strip of soft tissue. To implant graft 10, the middle of the strip (not shown) is first passed in a distal direction through a first tunnel 14 in the tibia into a second tunnel 18 in the femur, and then attached to the femur tunnel (or attached to bone adjacent the femur tunnel) with a femur fixation device (not shown). Two approximately equal length segments 19a, 19b of the graft extend proximally from the attached middle portion through tunnels 18 and 14. The two ends 20a, 20b of segments 19a, 19b terminate proximal to tibial tunnel 14. Segments 19a and 19b of the graft are then fixed within tibial tunnel 14 by inserting bone screw 12 between the two segments, such that shaft 22 of the screw presses the segments against internal wall 24 of tunnel 14.

In attaching soft tissue within a bone tunnel using a bone screw, it is important that the tissue be rigidly fixed within the tunnel to prevent slippage. When the bone involved is relatively soft (less calcified), a common problem in elderly patients, screws may not adequately fix the graft to the bone.

SUMMARY

According to one aspect, the invention features a sheath for organizing soft tissue including a first tube having a flexible body sized and shaped to receive a fixation device; and at least one second tube coupled to the first tube. The second tube has a flexible body sized and shaped to receive a soft tissue graft.

Embodiments of this aspect of the invention may including one or more of the following features.

A securing element secures the second tube to the soft tissue graft. The sheath includes a third tube coupled to the first tube having a flexible body sized and shaped to receive a soft tissue graft. At least one of the first tube and second tube is formed of a biocompatible material selected from the group consisting of hydroxyapatite, polylactic acid, and polylactic glycolic acid. A guide is disposed within the second tube for facilitating threading of soft tissue through the second tube. A guide is disposed within the first tube for facilitating advancement of a guide wire through the first tube. One end of the guide in the first tube has a funneled shape.

The first tube and the second tube are integrally formed. The flexible bodies of the tubes have strands that form a mesh structure. The strands defines spaces therebetween. The flexible bodies of the tubes include a relieved wall that is perforated and defines a plurality of holes therethrough. A major portion of the relieved wall is open. The flexible body of the second tube has two ends and each end has an opening. The two openings are circular and have substantially the same dimensions. The first tube is smaller in diameter than the second tube.

According to another aspect, the invention features an assembly including the sheath for organizing soft tissue and a fixation device. Embodiments of this aspect of the invention may include that the fixation device is a bone screw, and the flexible body of the first tube is conformable to a shape of the shaft of the bone screw.

According to another aspect, the invention features a method for implanting soft tissue in a bone tunnel. The method includes coupling a soft tissue graft to a sheath assembly; and positioning the sheath assembly relative to the soft tissue graft based on a measured depth of a bone tunnel.

Embodiments of this aspect of the invention may include one or more of the following features.

The method includes inserting the soft tissue graft and the sheath assembly into the bone tunnel, and inserting a fixation device into the sheath assembly to fix the sheath assembly and soft tissue graft inside the bone tunnel. The sheath assembly is fixed inside the bone tunnel such that an end of the sheath assembly is flush with an entrance to the bone tunnel. The method includes applying tension to the soft tissue grafts during the insertion of the soft tissue grafts. The method includes organizing a plurality of soft tissue grafts so an approximately equal tension can be applied to each graft.

Coupling a portion of a soft tissue graft includes inserting a portion of a soft tissue graft into the sheath assembly. The method includes providing the sheath assembly with a first tube including a flexible body sized and shaped to receive a fixation device and at least one second tube coupled to the first tube and sized and shaped to receive the soft tissue graft. The method includes inserting the fixation device, e.g., a bone screw, into the first tube to fix the soft tissue graft inside the bone tunnel.

According to another aspect, the invention features a set of surgical devices for implanting soft tissue grafts in a bone tunnel. The set includes a sheath assembly including a first tube and at least one second tube. The first tube is sized and shaped to receive a fixation device and the second tube is sized and shaped to receive a soft tissue graft. The set includes a measurement device for measuring the depth of the bone tunnel; and a securing element configured to secure the sheath assembly to the soft tissue graft at a position determined by the measured bone tunnel depth.

Embodiments of this aspect of the invention may include one or more of the following features.

The set includes a device configured to organize a plurality of soft tissue grafts. The device includes a member having a first section and a second section. The member is configured such that a first soft tissue graft is securable to the first section and a second soft tissue graft is securable to the second section in response to manipulation of only the first section.

The securing element, e.g., a tie suture, is attached to the sheath assembly.

According to another aspect, the invention features a device for securing soft tissue grafts. The device includes a member having a first section and a second section. The member is configured such that a first soft tissue graft is securable to the first section and a second soft tissue graft is securable to the second section in response to manipulation of only the first section.

Embodiments of this aspect of the invention may include one or more of the following features.

The member includes a first knob disposed on the first section and a second knob disposed on the second section. The first knob is knurled and manipulation of the first end is turning the first knob. A mating member is disposed on the first section and is configured to mate with the first knob. The second section includes a mating surface configured to mate with the second knob. A first spring is positioned between the mating member and first knob, and a second spring is positioned between the mating surface and the second knob.

In an illustrated embodiment, a second member is coupled to the first member. The second member has a first section and a second section. The second member is configured such that a third soft tissue graft is securable to the first section and a fourth soft tissue graft is securable to the second section in response to manipulation of only the first section.

The invention may include one or more of the following advantages.

The flexibility and thinness of certain implementations of the sheath allows the sheath to conform, e.g., to the shape of the fixation device, or to the shape of a bone tunnel.

The relief in the sheath, e.g., perforations in a wall of the sheath, allows in situ contact between a soft tissue graft and the wall of a bone tunnel, promoting development of Sharpy-like fibers and permanent attachment of the soft tissue to the bone.

Therapeutic agents, such as osteoinductors or growth factors, can be disposed on or embedded into the material of the sheath, allowing delivery of the agent directly to the site of fixation.

Sheath implementations with multiple tubes allow multiple soft tissue grafts to be fixed into a bone tunnel. The securing element may be used to facilitate insertion of sheaths with multiple tubes by decreasing the area of the cross-section of the inserted sheath and grafts, and by fixing the sheath in place on the grafts. Guide tubes may be used to facilitate insertion of grafts into the flexible tubes of the sheaths.

The tensioner device allows tension to be equalized among multiple grafts and organizes the grafts to permit easy introduction of a fixation member. The tensioner device decreases the amount of work required to secure grafts by allowing two grafts to be secured to the tensioning device at opposite ends of the tensioning device substantially simultaneously through the manipulation of only one knob. This allows the surgeon to hold two separate tendons and simultaneously lock the tendons in place without requiring assistance from another person.

Other implementations and advantages of the invention will be apparent from the following description and from the claims.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 13 is a perspective view of a sheath of the kit of FIG. 12;

FIG. 14 is a perspective view of a sheath assembly including the sheath of FIG. 13, guides, and a suture of the kit of FIG. 12;

FIG. 15A is a perspective view of an adjustable stop for a bone depth measurement device of the kit of FIG. 12;

FIG. 15B is a cross-sectional view of the adjustable stop of FIG. 15A;

Like reference symbols in the various drawings indicate like elements.

DETAILED DESCRIPTION

Embodiments of the invention feature sheaths that surround bone screws and soft tissue grafts to improve fixation of the grafts. In its simplest form, the sheath is a flexible, mesh tube that surrounds only the bone screw, both the bone screw and the graft, or only the graft. In other embodiments, the sheath includes multiple tubes.

Figure 1:
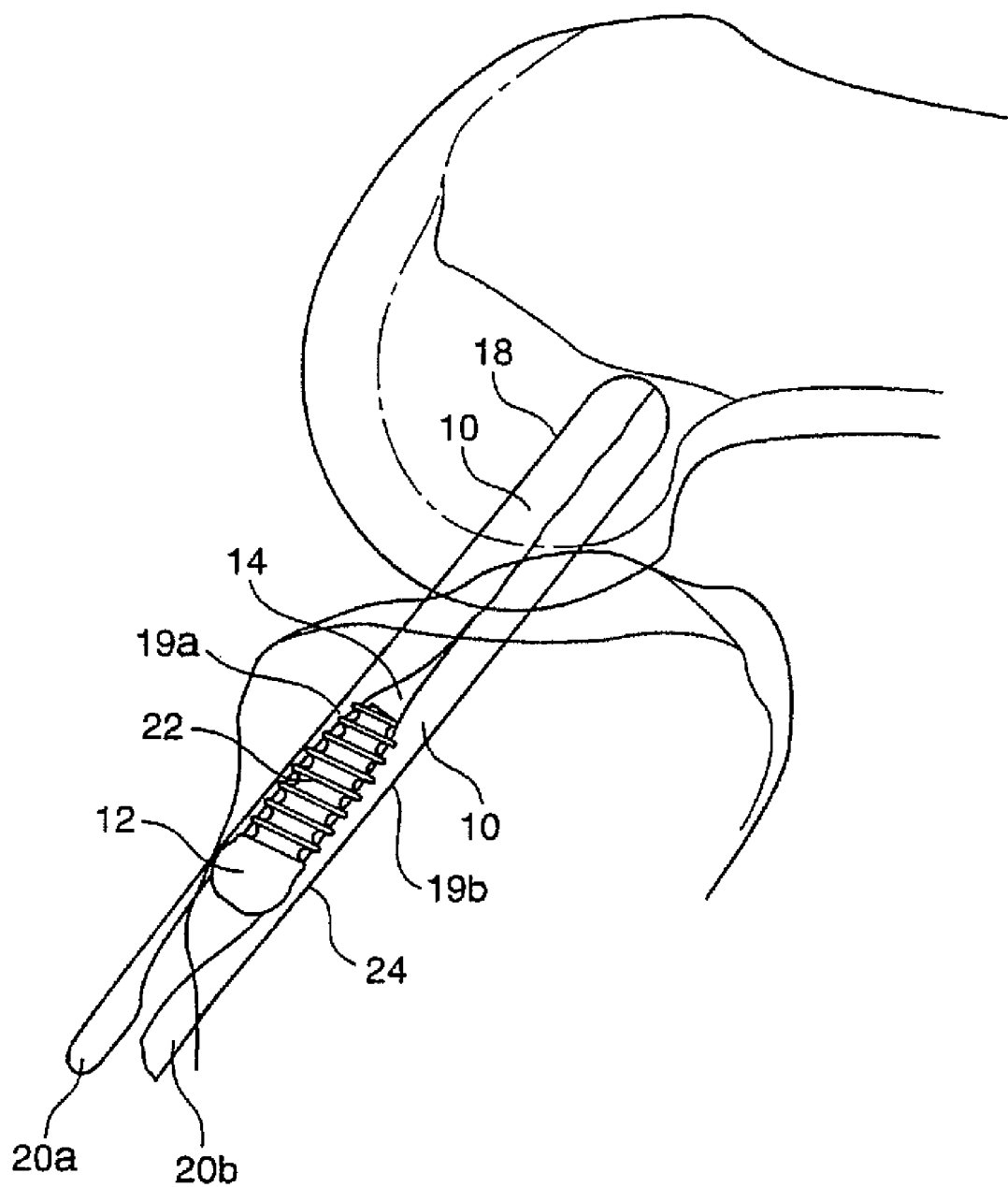
FIG. 1 is a sectional view of a prior art technique of fixing a ligament graft within a tibial bone tunnel by using a bone screw.
Figure 2A:
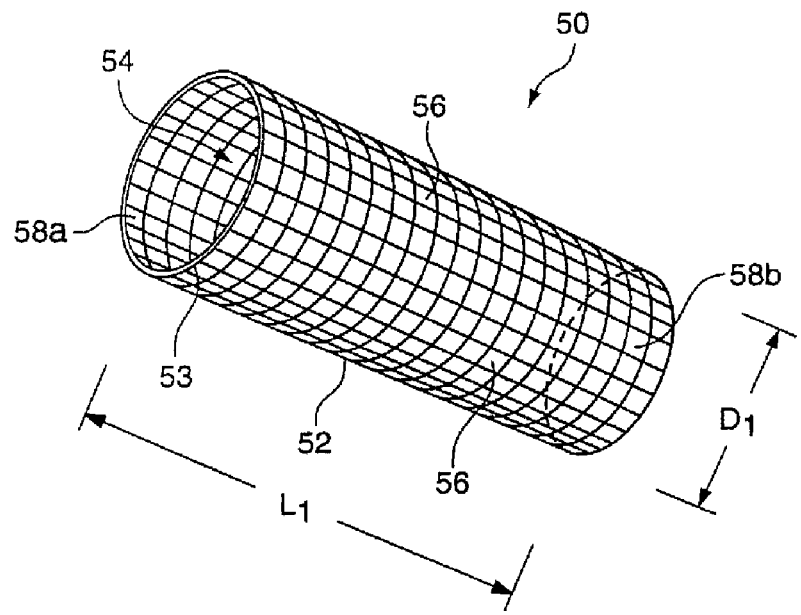
FIG. 2A is a perspective view of a bone screw sheath.
Figure 2B:
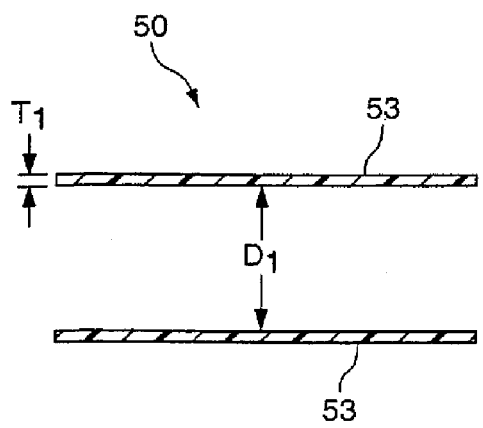
FIG. 2B is a sectional view of the bone screw sheath of FIG. 2A.
Figure 2C:
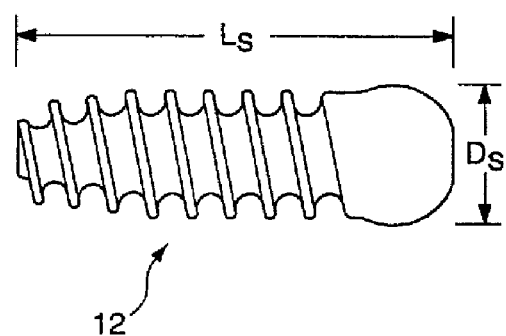
FIG. 2C is a sectional view of the bone screw of FIG. 1.

Referring to FIGS. 2A-2C, a sheath 50 has a tube-shaped body 52 that defines a generally cylindrical exterior surface 53 and a generally cylindrical interior 54. Body 52 is formed from a biocompatible material woven into a mesh structure. The mesh defines numerous holes 56 that expose interior 54 to the outside. Sheath 50 also has two circular, open ends 58a, 58b, allowing a tissue graft to pass entirely through the interior of the sheath.

Interior 54 of sheath 50 is sized and shaped to receive bone screw 12. Sheath 50 has an internal diameter D1 greater than the diameter DS of bone screw 12, so that both screw 12 and segments 19a and 19b of graft 10 can fit snugly within the sheath. The sheath has a length L1 slightly larger than the length LS of screw 12. The mesh body 52 is thin and flexible, allowing the sheath to adjust to snugly surround the screw; body 52 can be compressed to reduce the volume of interior 54, twisted, or stretched. Since sheath 50 is thin and flexible rather than rigid, it cannot on its own shore up soft bone, or fix a graft within a bone tunnel. (I.e., sheath 50 is not designed to be used alone as a fixation device or as a solid, rigid reinforcement of soft bone.)

In some embodiments, the threads forming the mesh body 52 are larger in the radial direction than in the axial direction. This difference in thread size results in sheath 50 being less flexible radially than axially. In these embodiments, the diameter D1 is more resistant to expansion or contraction than length L1. In other embodiments, the thread size is equal throughout body 52.

Diameter D1 is, e.g., between about 8 and 10 mm, and L1 is, between about 25 and 40 mm. If sheath 50 is designed for a 7×25 bone screw (7 mm diameter, 25 mm length), then L1 is, e.g., about 30 mm, and D1 is, e.g., about 9 mm. Most of exterior surface 53 is open. For example, about 40% of the area exterior surface 53 is mesh strands, and about 60% is holes 56. The thickness T1 of the mesh wall of sheath 50 is, for example, less than about 0.3 mm, e.g., about 0.1-0.2 mm.

Body 52 can be made from a variety of bioabsorbable materials, including polylactic acid, or polylactic glycolic acid. Alternatively, body 52 can be made from a blend of absorbable materials, or from a non-absorbable material, such as a polyester. The material forming the body preferably has a higher coefficient of friction than graft 10, so that exterior surface 53 of the sheath grips internal wall 24 of bone tunnel 14 more firmly than graft 10 alone, improving fixation.

Body 52 can be formed, e.g., by weaving, braiding, knitting, or crocheting strands of the material to form the cylindrical shape, or by extrusion, using techniques known in the art. The strands forming body 52 have diameters of about 0.1-1.0 mm, e.g., 0.4-0.6 mm, or 0.51 mm.

Although sheath 50 can be used with a variety of fixation screws, screw 12 preferably has blunt or rounded screw threads, as opposed to sharp threads, so that the threads do not cut the sheath or the soft tissue graft. A typical rounded-thread screw is shown in Roger et al., U.S. Pat. No. 5,383,878, which is incorporated herein by reference.

Figure 3:
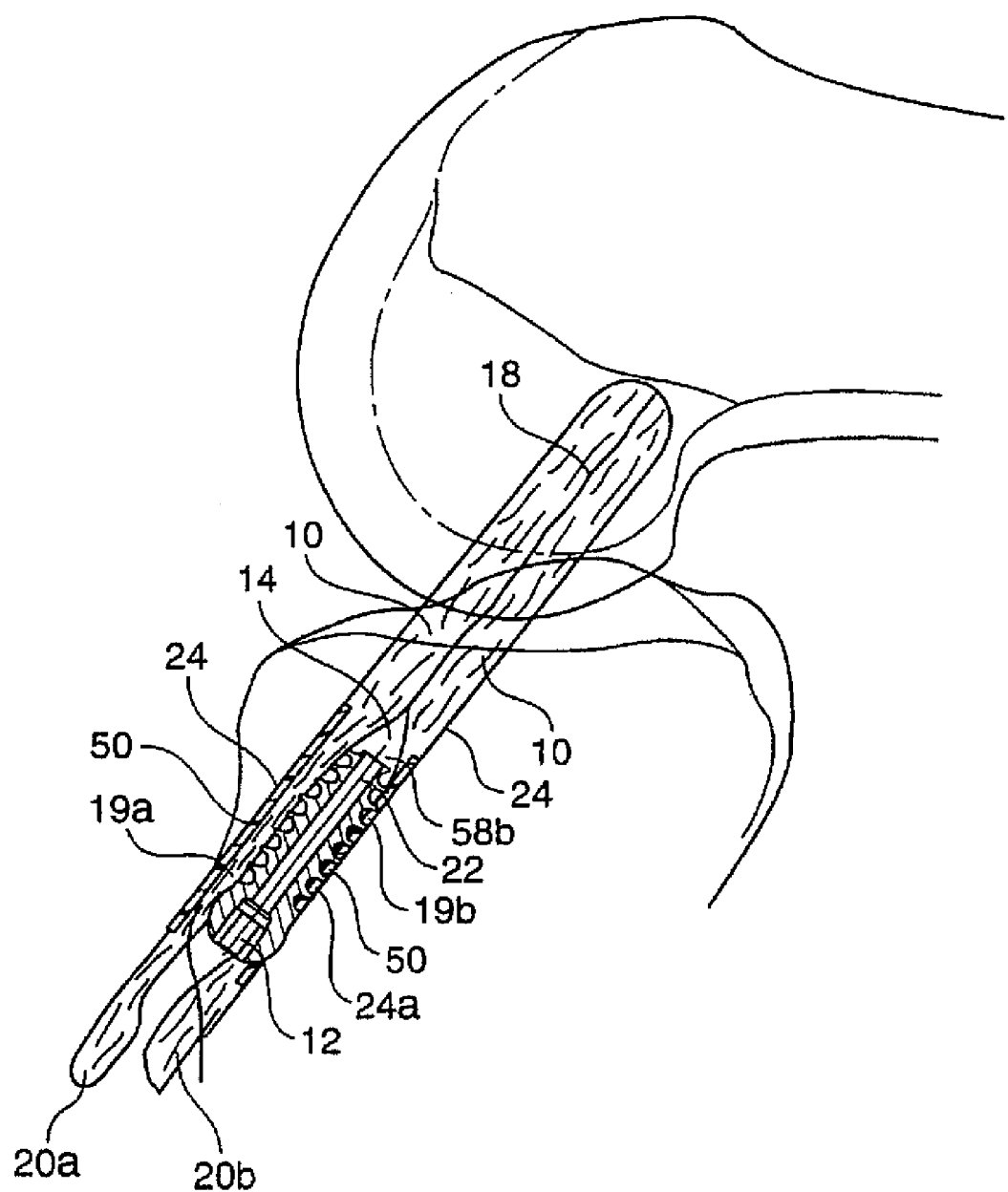
FIG. 3 is a sectional view of a the bone screw and sheath of FIGS. 2A-2C fixing a ligament graft within a bone tunnel in the tibia.

Referring to FIG. 3, in operation, a surgeon first forms bone tunnels 14 and 18 within the tibia and femur, respectively. Next, graft 10 is fixed to the femur tunnel using any technique known in the art (not shown). For example, the femur fixation device can include a loop attached to the femur at a distal end of femur tunnel 18. End 20a of the graft is passed distally through tunnels 14 and 18, passed through the loop, and then pulled proximally through tunnels 18 and 14 until the middle portion of the graft is centered on the loop. Alternatively, the graft can be threaded through the loop prior to implantation of the loop. In addition, rather than using a loop, one end of graft 10 can be fixed within the femur tunnel, allowing the other end to extend proximally through tunnels 18 and 14. To increase the number of segments available for fixation, multiple strips of soft tissue (i.e., multiple grafts) can be separately attached to the femur. Various techniques for attaching a graft within a bone tunnel are described in Ferragamo, U.S. Pat. No. 5,769,894, which is incorporated herein by reference, and in Rosenberg, supra.

After attaching graft 10 within (or adjacent to) femur tunnel 18, the surgeon passes ends 20a, 20b of graft 10 through interior 54 of sheath 50 (via open ends 58a and 58b), and then slides sheath 50 into tibial tunnel 14. The diameter of tunnel 14 is only slightly larger than the outer diameter of sheath 50, such that sheath 50 fits snugly within tunnel 14. Alternatively, sheath 50 can be inserted into tunnel 14 prior to passing the graft through the sheath. To insert sheath 50 into tibial tunnel 14, the surgeon can use a delivery tool, such as a rigid tube detachably fixed to the distal end of the sheath. Alternatively, a suture can be threaded through the distal end of sheath 50, and the sheath can be pulled into place within tunnel 14 using the suture.

The surgeon then inserts bone screw 12 into interior 54 of sheath 50, between segments 19a and 19b of the graft. The screw may be inserted using an insertion tool known in the art, such as a screw driver. When screw 12 is in place as shown in FIG. 3, the screw presses segments 19a and 19b of the graft against the interior surface of sheath 50, and presses exterior surface 53 of the sheath against wall 24, fixing the graft within the tunnel.

As shown in FIG. 3, when screw 12 is inserted, it will typically be slightly off center, such that the screw's threads dig into wall 24 of bone tunnel 14 along a segment 24a of wall 24. For example, if screw 12 has a major diameter of 9 mm, and a minor diameter of 7 mm, then the screw threads will dig into wall 24 by about 1 mm along segment 24a, where segment 24a is about 120 degrees. This engagement of the threads with segment 24a of the wall helps hold screw 12 within tunnel 14, and therefore improves fixation of graft 10 within the tunnel.

The presence of sheath 50 within bone tunnel 14 improves fixation of graft 10. Since exterior surface 53 of sheath 50 has a higher coefficient of friction than graft 10, sheath 50 is less likely than graft 10 (which is made of tissue) to slide along wall 24 of the tunnel, or to twist when screw 12 is inserted into the tunnel. In addition, since body 52 of sheath 50 has a mesh structure, portions of graft 10 protrude through holes 56 of the mesh, resisting sliding of graft 10 relative to sheath 50. The flexibility of sheath 50 allows the sheath to conform to the shape of wall 24, maximizing the surface area contact between the exterior surface of the sheath and wall 24, thereby increasing frictional forces between the sheath and the wall.

After screw 12 has been inserted into tunnel 14, the surgeon may trim the portions of segments 19a and 19b that extrude proximally from tunnel 14, completing the surgical procedure. Over time, graft 10 permanently affixes to wall 24 by growth of Sharpy-like fibers between the soft tissue of graft 10 and the bone tissue of wall 24. ("Sharpy-like fibers" are collagenous fibers that grow from bone into a soft tissue graft. The presence of Sharpy-like fibers indicate good bony growth to the graft, and therefore good fixation. See Pinczewski et al., "Integration of Hamstring Tendon Graft With Bone in Reconstruction of the Anterior Cruciate Ligament," *Arthroscopy*, 13: 641-43 (1997). The open holes 56 in body 52 of the sheath facilitate permanent fixation by increasing the direct contact between the graft and the bone tunnel wall. Sheath 50 eventually dissolves, and new bone grows to fill its position.

To accelerate bone growth and permanent attachment of graft 10 to wall 24, sheath 50 can include an osteoinductive agent, such as hydroxyapaptite, tricalcium phosphate, calcium sulphate, or a "ceramic" (a calcium and potassium crystalline). The osteoinductive agent can be applied to sheath 50 prior to surgery by, e.g., spraying the sheath with the agent, by dipping the sheath into a bath that includes the agent, by dusting or spraying the agent onto the sheath, or by filling the sheath with a gel that includes the agent. In addition, the strands of material forming the mesh body 52 can be hollow, and the agent can be within the hollow interiors of the strands. Alternatively, the agent can be incorporated into the material that forms body 52. For example, the agent can be blended into the material used to make the threads that form mesh body 52, or can be added to the fibers as an osteoinductive felt.

Other therapeutic agents, such as growth factors (e.g., tissue growth factor or platelet derived growth factor), bone morphogenic proteins, stem cells, osteoblasts, and cytokines, can also be included in the sheath. These bioactive agents can be added using the techniques described above, or can be blended into the material that forms body 52 using microencapsulation or nanoparticles. For example, body 52 can be formed from a material comprising microspheres of the agent and a polymer, such as polylactic glycolic acid. The microspheres of the agent and polymer can be prepared using known techniques. See, e.g., Cohen et al., "Controlled Delivery Systems for Proteins Based on Poly(Lactic/Glycolic Acid) Microspheres," *Pharm. Research*, 8:713-20 (1991); DeLuca et al., U.S. Pat. Nos. 5,160,745 and 4,741,872. Rather than forming microspheres, the agent and polymer can also be mixed together using, e.g., sintering techniques. See, Cohen et al., "Sintering Techniques for the Preparation of Polymer Matrices for the Controlled Release of Macromolecules," *J. Pharm. Sciences*, 73:1034-37 (1984). The bioactive agents can also be attached to body 52 using adhesives or electrical charge, or can be directly loaded onto the sheath by a delivery mechanism after implantation of the sheath.

Other embodiments are within the scope of the claims. For example, the sheath can be used to assist fixation of a bone screw within the femur tunnel 18, in addition to the tibial tunnel 14.

Figure 4:
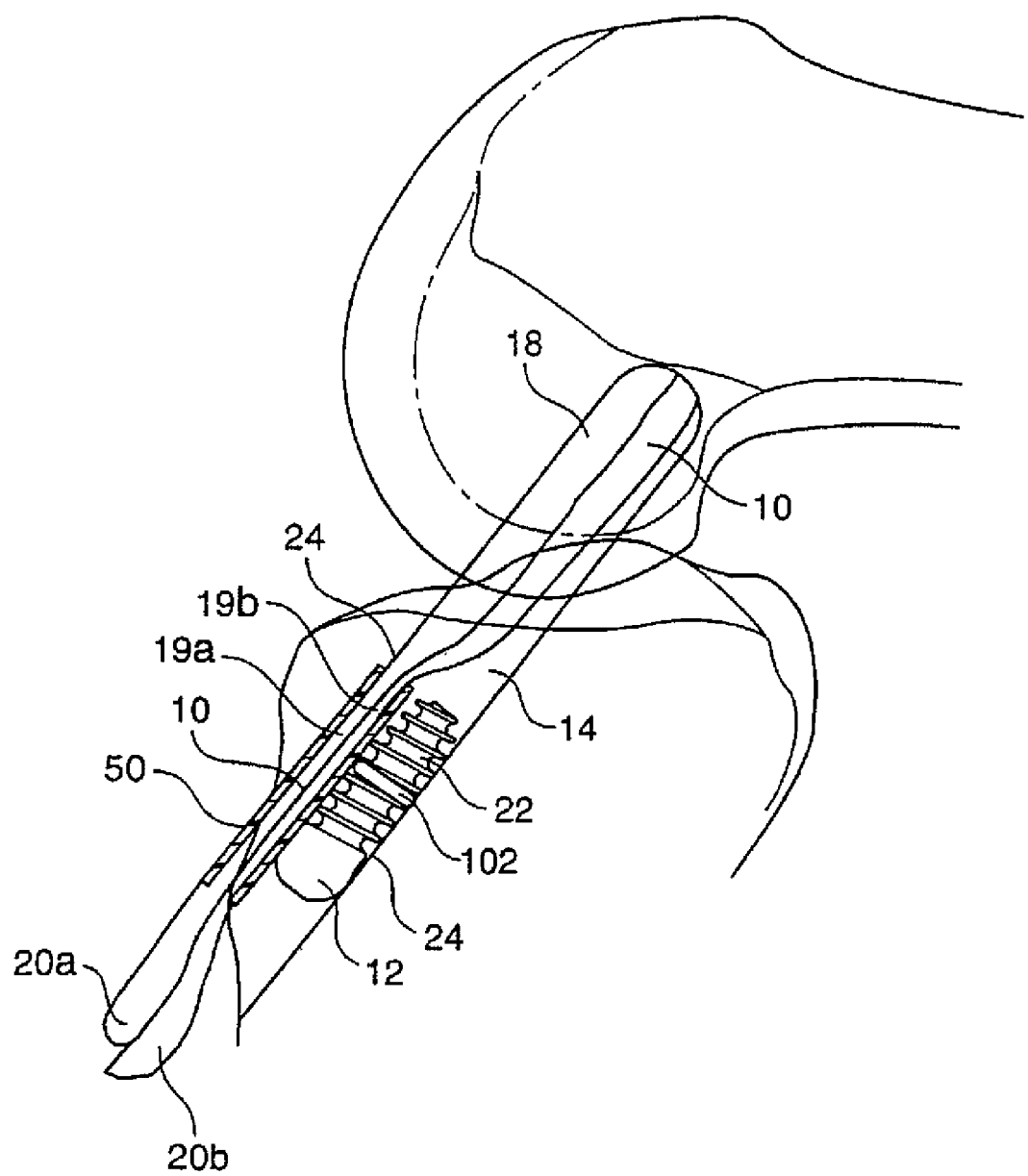
FIGS. 4 and 5 are sectional views illustrating alternative arrangements for the bone screw, sheath, and graft of FIG. 3 within the bone tunnel in the tibia.

Referring to FIG. 4, screw 12 can be placed between sheath 50 and wall 24 of tunnel 14. In this embodiment, rather than inserting screw 12 into the sheath after placement of the sheath within tunnel 14, screw 12 is inserted into tunnel 14 along the side of the sheath. To hold screw 12 to the side of the sheath, the sheath can optionally include an external loop 102. Loop 102 has a diameter slightly larger than the diameter of screw 12, so that shaft 22 of screw 12 fits snugly within the loop. Loop 102 can be made from the same material as body 52, or can be made from an inflexible, rigid material.

When screw 12 is inserted, it compresses graft 10 within the sheath, and presses exterior surface 53 of the sheath against wall 24, fixing graft 10 within tunnel 14.

Figure 5:
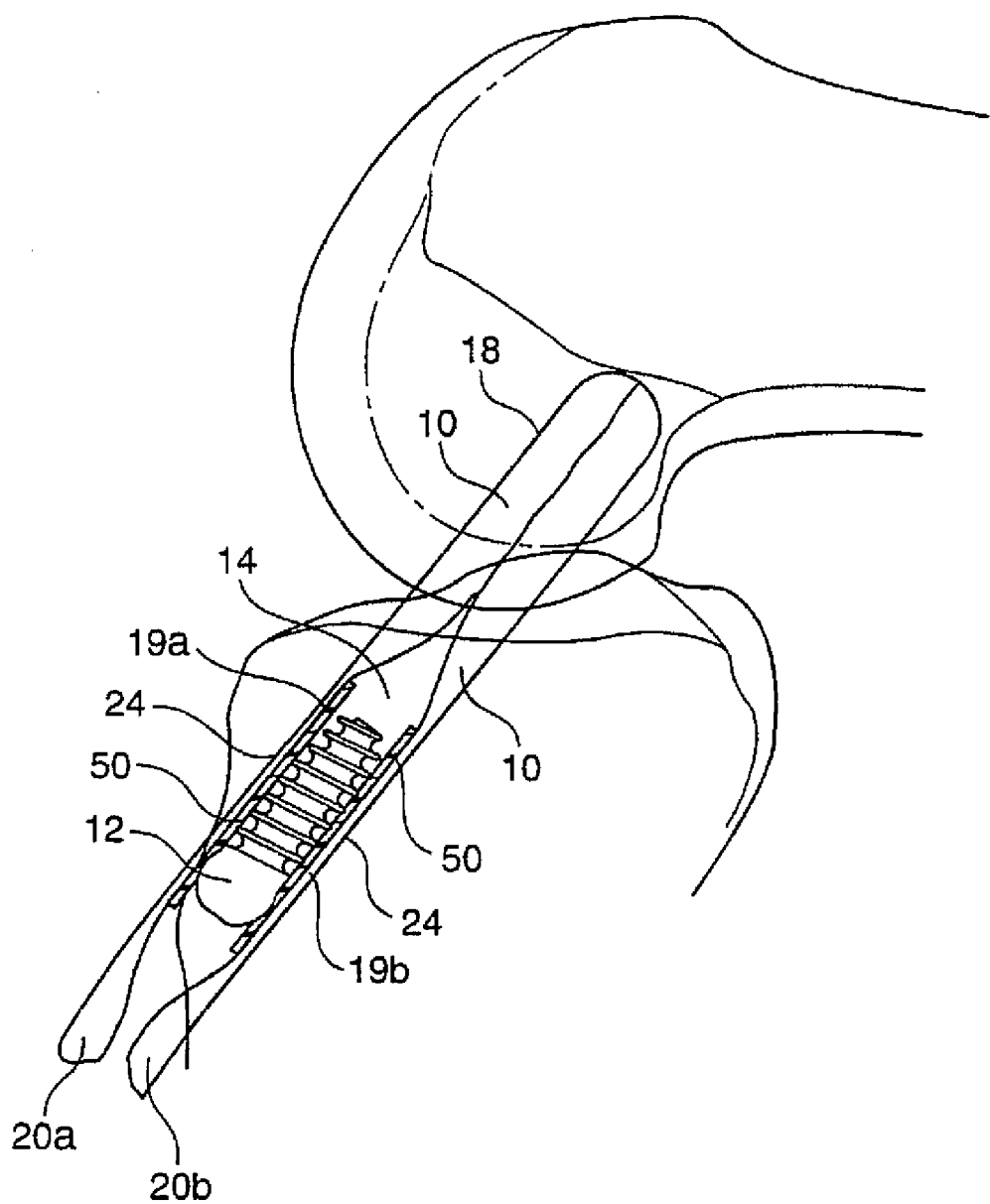

Referring to FIG. 5, segments 19a and 19b of graft 10 can be positioned radially outside of sheath 50. In this embodiment, when sheath 50 is inserted into tunnel 14, it is located between ends 19a and 19b of the graft, so that the graft surrounds the sheath, rather than the sheath surrounding the graft. Screw 12 is then inserted into the sheath, pressing segments 19a and 19b between exterior surface 53 of the sheath and wall 24, fixing the graph in place. Alternatively, the screw can first be inserted into the sheath, and then the sheath and screw together can be positioned within the bone tunnel.

The structure of the bone screw sheath can be modified as well. The diameter $D_1$, length L1, and thickness T of the sheath can be varied to accommodate different sized bone tunnels, different sized screws, and different deployment methods. For example, in the deployment method of FIG. 5, the inner diameter $D_1$ of the sheath can be approximately equal to the diameter $D_S$ of the screw shaft, so that the screw fits very snugly within the sheath, and exterior surface 53 of the sheath conforms to the shape of the screw shaft.

In the deployment methods shown in FIGS. 4 and 5, the sheath need not be more rigid in the radial direction than in the axial direction. The threads forming the mesh body, therefore, are generally the same size in both the radial and axial directions. In addition, sheaths used in the deployment method of FIG. 5 can have less open space than sheaths used with the method of FIG. 3 or 4. (i.e., less than 60% of the sheath's surface area will be holes.)

If the bone is particularly soft, sheath 50 can be woven tighter, so that the sheath is less flexible, thereby providing a more firm substrate for screw 12 to engage.

The sheath need not have a mesh structure. For example, the sheath can have a solid body with holes cut through the body, allowing communication between the exterior and interior of the sheath. In addition, the sheath's body need not be integrally formed. For example, the body can be formed by winding a strip of material around an implantable device to form a relieved body that defines an interior.

The sheath can have relief structures other than holes to allow communication between the exterior and interior. For example, other types of perforations, such as slits, can be used, instead of holes. In addition, the device can have a solid wall with thinned sections. When implanted, the thinned sections biodegrade more quickly than other sections of the wall, such that in situ, the device develops perforations.

To increase the coefficient of friction of exterior surface 53 to improve fixation of the sheath within the bone tunnel, exterior surface 53 can have a roughened finish.

Figure 6:
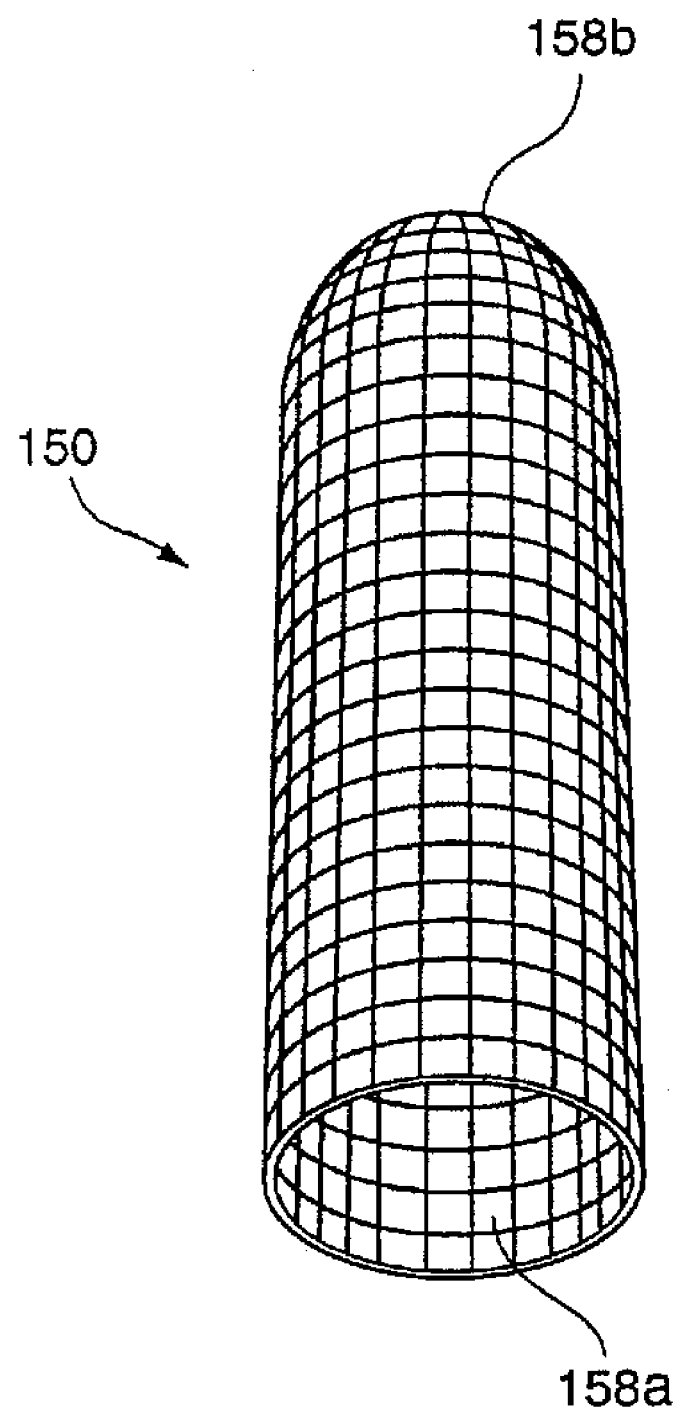
FIG. 6 is a perspective view of an alternative embodiment of the sheath of FIG. 2A.

Referring to FIG. 6, rather than having two open circular ends, sheath 150 has an open end 158a and a closed end 158b. Closed end 158b gives sheath a "bag" or "sock" shaped structure.

Figure 7A:
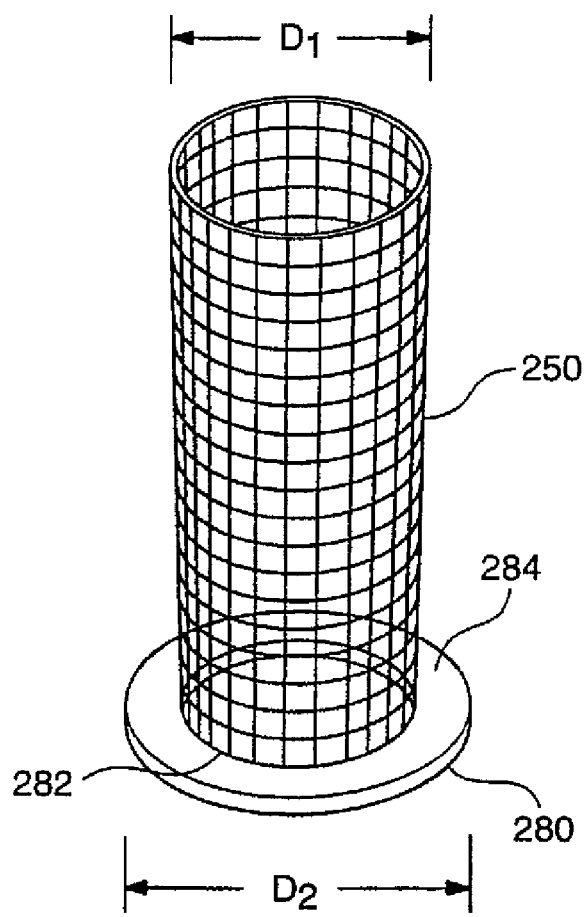
FIG. 7A is a perspective view of an alternative embodiment of the sheath of FIG. 2A that includes a washer.
Figure 7B:
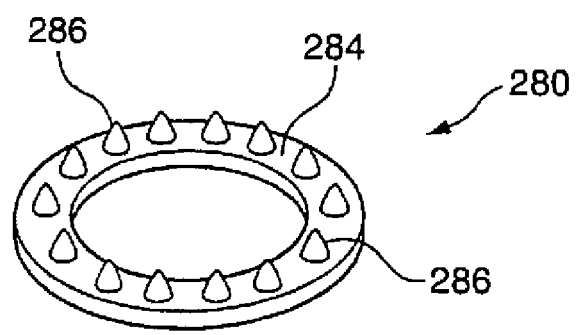
FIG. 7B is a top view of the washer of FIG. 7A.

Referring to FIG. 7A, a sheath 250 includes a washer 280 attached to the proximal end 282 of the sheath. The washer 280 has a diameter D2 that is larger than diameter $D_1$ of sheath 250, and is larger than the diameter of the bone tunnel. Washer 280 prevents proximal end 282 of the sheath from passing into the bone tunnel when the screw is inserted into the sheath, thereby ensuring that the sheath is ultimately positioned around the screw shaft, rather than in front of the screw. Rather than being circular, the washer can be square, triangular, or any other shape, so long as it has a dimension larger than the diameter of the bone tunnel. Referring to FIG. 7B, the upper surface 284 of the washer can include teeth or spikes 286 to grip bone, thereby reducing twisting of sheath 250 when a bone screw is inserted into the sheath. The washer can be made from a bioabsorbable material, or a non-absorbable, biocompatible material. In operation, the washer can be detached from the sheath after implantation of the graft and bone screw, or can be left attached to the sheath.

Figure 8:
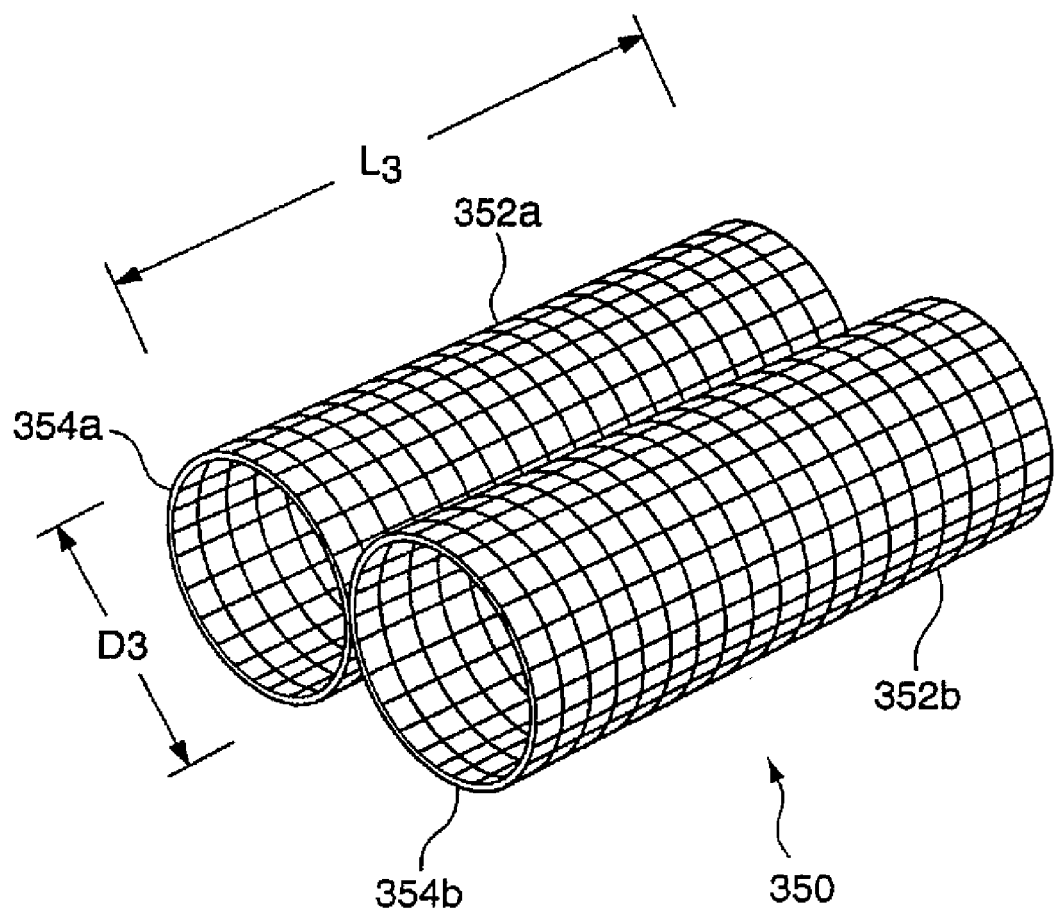
FIG. 8 is a perspective view of an alternative bone screw sheath that includes two tubes.

Referring to FIG. 8, a sheath 350 includes two contiguous, parallel mesh tubes, 352a and 352b. Tubes 352a and 352b are integrally woven, braided, knitted, or crocheted from threads. Each tube has a diameter $D_3$ that is slightly larger than diameter Ds of screw 12, and slightly less than diameter $D_1$ of sheath 50. Diameter $D_3$ can be, e.g., 2 mm, 4 mm, 6 mm, or 8 mm. Sheath 50 has a length L3 approximately equal to the length of a fixation screw, e.g., about 10-50 mm, or 20-35 mm. The walls 354a, 354b of tubes 352a and 352b each have a thickness of, e.g., between 0.1 mm and 1.0 mm.

In operation, a soft tissue graft is passed through one of the tubes (e.g., tube 352a), and the fixation screw is inserted into the second tube (e.g., tube 352b). When the sheath, graft, and fixation screw are positioned within the bone tunnel, tube 352a is compressed between the screw and a wall of the bone tunnel. The graft, therefore, is compressed within tube 352a, fixing the graft within the bone tunnel.

Figure 9:
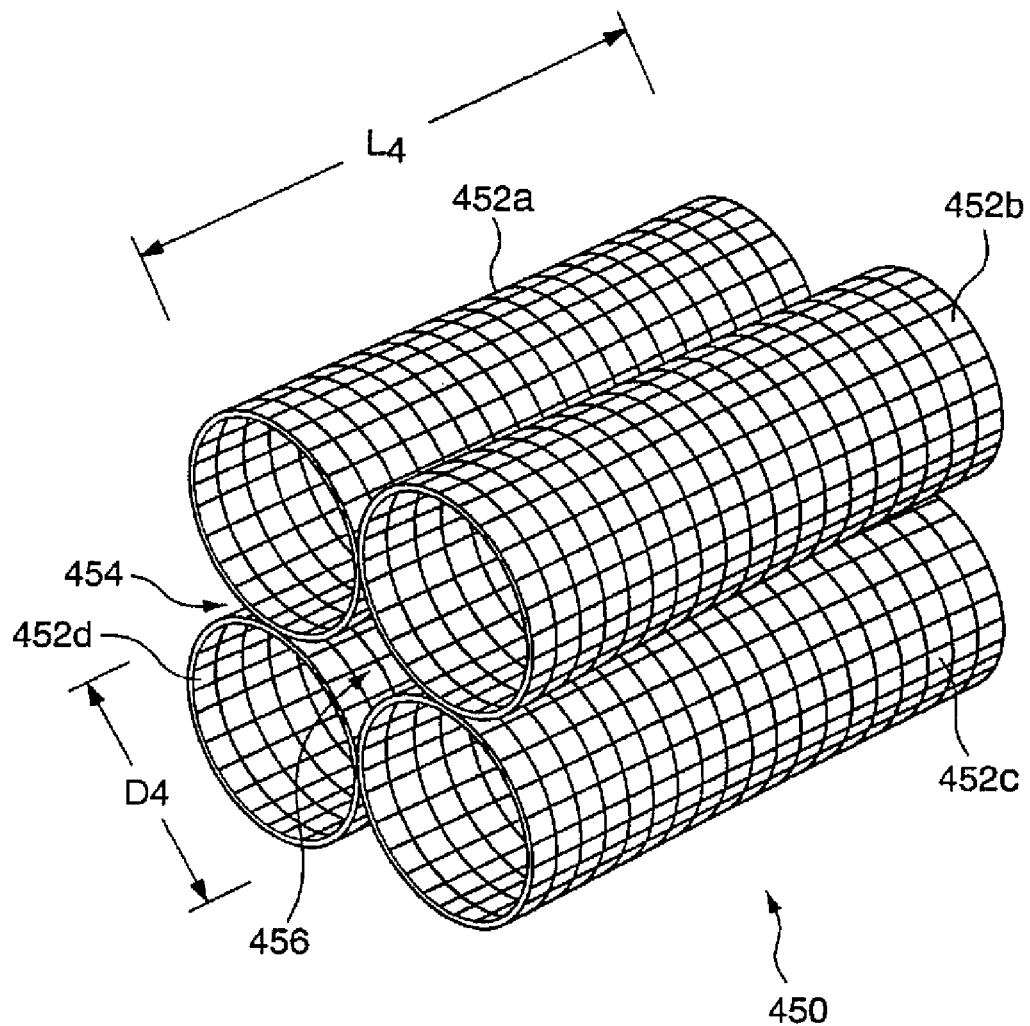
FIG. 9 is a perspective view of an alternative bone screw sheath that includes four tubes arranged to form a ring.

Referring to FIG. 9, a sheath 450 includes four parallel mesh tubes, 452a, 452b, 452c, and 452d. The four tubes are arranged to form a ring 454. Ring 454 defines a central cavity 456 disposed between the tubes. The cavity defines an axial bore that is coextensive with the axial lengths of each of the tubes.

Each tube 452a, 452b, 452c, and 452d has a diameter $D_4$ and a length $L_4$ similar to diameter $D_3$ and length $L_3$ of sheath 350 (FIG. 8). As with sheath 350, the tubes of sheath 450 are integrally woven.

In operation, segments of a soft tissue graft are passed through each of tubes 452a-452d. The surgeon can either use multiple, independent tissue grafts separately attached to the femur tunnel, or can split the proximal end of a single graft into four separate segments. The sheath is then inserted into the tibial bone tunnel, and a fixation screw is inserted into central cavity 456. When the sheath, soft tissue, and screw are in place within the bone tunnel, the tubes are compressed between the screw and the bone tunnel wall, and the soft tissue segments are compressed within each tube, thereby fixing the soft tissue within the bone tunnel.

In the embodiment shown in FIG. 9, sheath 450 includes four tubes forming a ring. The sheath need not, however, be limited to this number. For example, the sheath can include a ring of 3, 5, 6, 7, or 8 tubes. In addition, soft tissue need not be passed through each tube. For example, soft tissue segments can be passed through two tubes, leaving the remaining tubes unoccupied.

Instead of being integrally woven, the tubes of sheath 450 can be woven, braided, or knitted separately, and attached together using, e.g., stitching, spot welding, or an adhesive. The tubes can also be solid rather than mesh, and need not all have the same diameter. In addition, unlike the single tube sheaths of FIGS. 2A, 6, and 7, sheath 450 can be rigid, rather than flexible.

Figure 10:
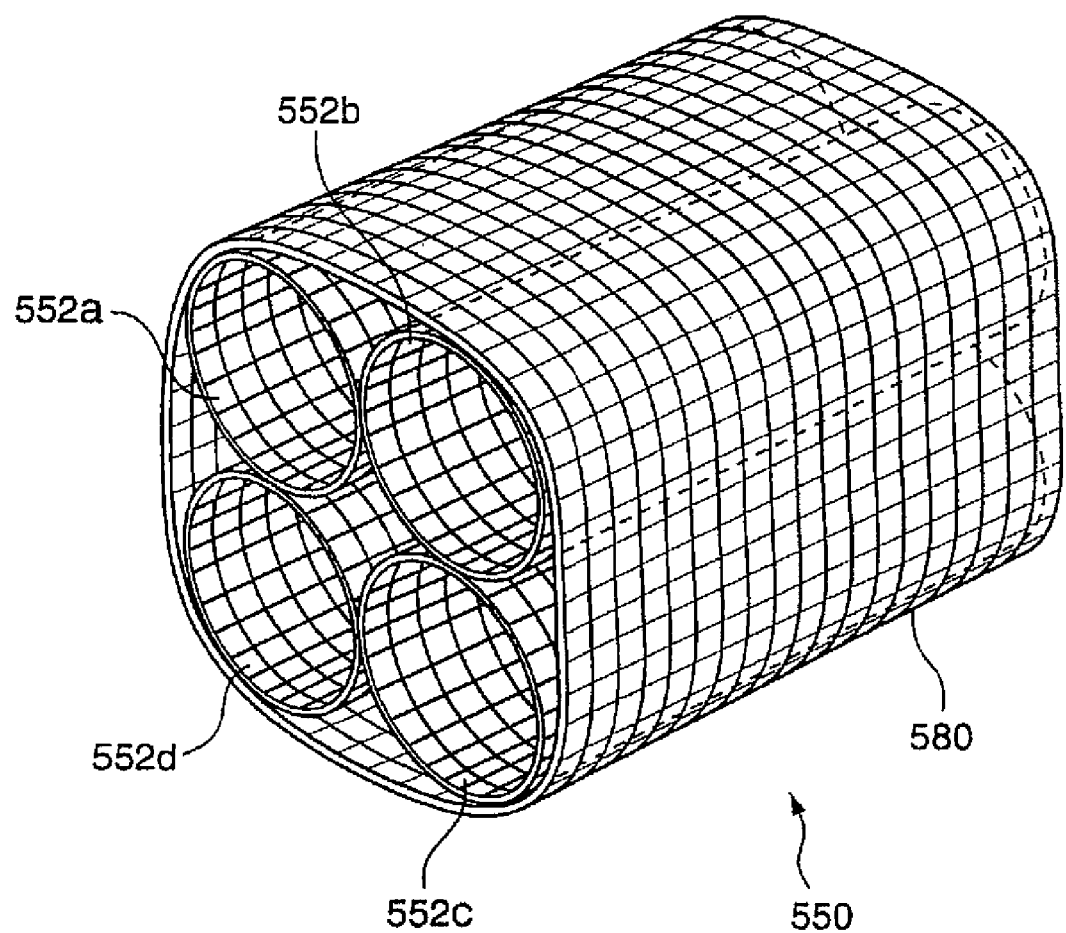
FIG. 10 is a perspective view of the bone screw sheath of FIG. 9 with an external sleeve.

Referring to FIG. 10, sheath 550 is identical to sheath 450 in all respects, except that sheath 550 further includes a mesh sleeve 580 that surrounds the four tubes 552a-552d. Sleeve 580 is axially coextensive with tubes 552a-552d, and is integrally woven with the four tubes. Alternatively, sleeve 580 can be a separate solid or mesh structure adhesively bound or otherwise coupled to the four tubes. Sleeve 580 acts to stabilize sheath 550, and facilitates insertion of the sheath into the bone tunnel. For example, to insert sheath 550, a suture or delivery tool can be attached to sleeve 580, rather than directly to one of the tubes.

Figure 11:
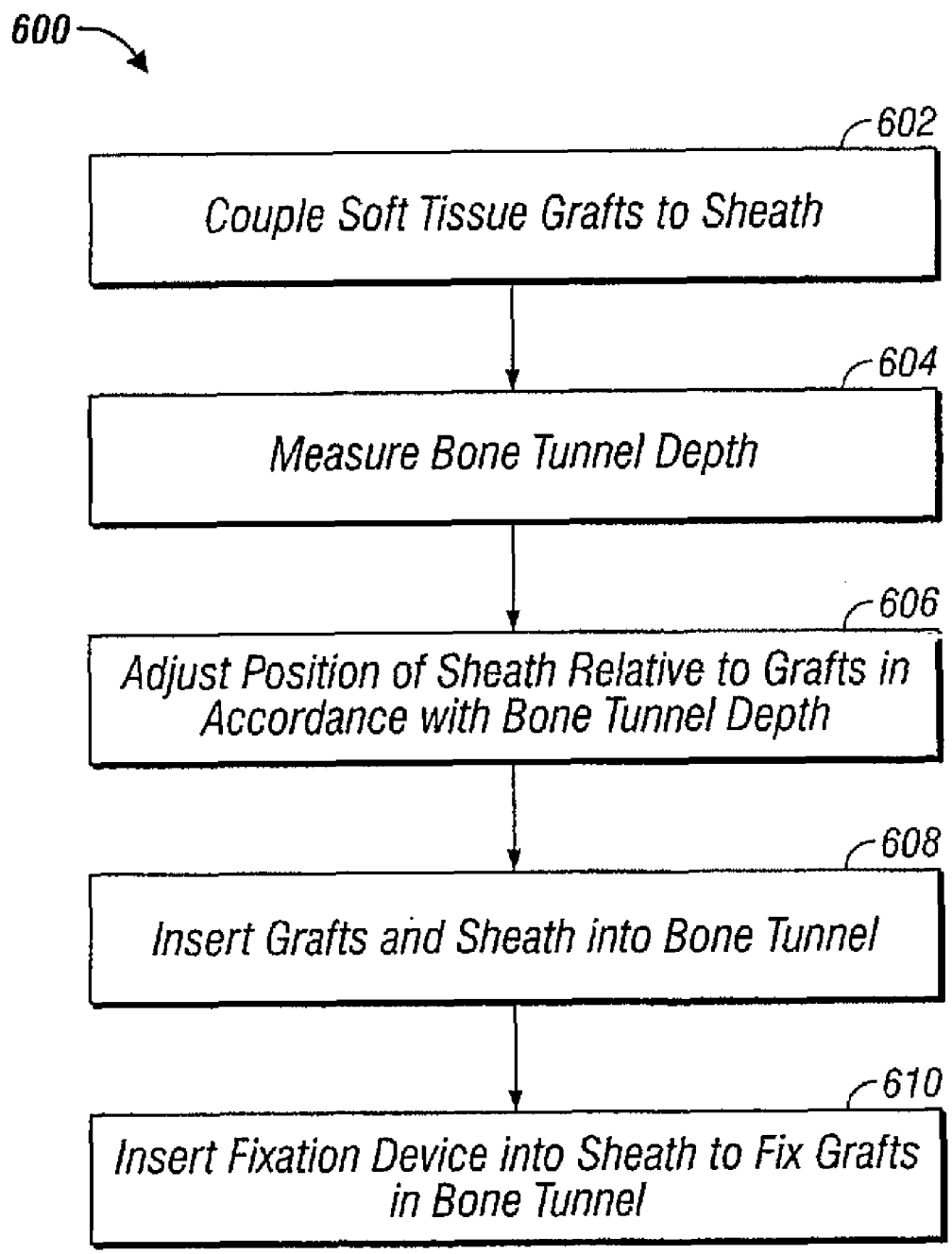
FIG. 11 is a flow chart of a surgical process to implant and fix soft tissue grafts in a bone tunnel using a sheath.

FIG. 11 shows a flow chart of a surgical process 600 to implant and fix soft tissue grafts in a bone tunnel using a sheath. After soft tissue grafts have been harvested in the usual fashion or otherwise acquired, the soft tissue grafts are coupled to the sheath (602), e.g., by inserting the grafts into the sheath and/or placing the grafts adjacent to the sheath. Concurrent, subsequent, or prior to coupling the grafts to the sheath, the bone tunnel depth is measured (604).

The position of the sheath relative to the grafts is adjusted in accordance with the measured depth of the bone tunnel (606). Adjustment of the position of the sheath ensures that the sheath, once inserted into the bone tunnel, is properly positioned in the bone tunnel to receive the fixation device used to fix the grafts and sheath in the bone tunnel. For example, when the fixation device is a typical interference screw, the sheath is preferably placed such that one end of the sheath is flush with the entrance of the bone tunnel. To properly position the sheath relative to the grafts, the adjustment of the position of the sheath in accordance with the measured depth of the bone tunnel is preferably carried out while the grafts are placed under a tensile load similar to that experienced by the grafts after fixation in the bone tunnel. Once properly positioned, the sheath is fixed to the grafts to prevent movement of the sheath relative to the grafts during insertion into the bone tunnel (608) and after fixation of the sheath and graft assembly in the bone tunnel.

After insertion of the sheath and graft assembly into the bone tunnel, a fixation device, e.g., a bone screw, is inserted into the bone tunnel and is received by the sheath to fix the sheath and graft assembly in the bone tunnel (610). In another implementation, the graft is inserted first into the bone tunnel, and the sheath is subsequently pushed up into the tunnel using an insertion tool.

More than one sheath can be coupled to a given graft and positioned relative to the graft in accordance with the bone tunnel depth. For example, in ACL replacement surgery, a first sheath coupled to the grafts is positioned within the femoral side tunnel, and a second sheath coupled to the grafts is positioned within the tibial side tunnel.

Figure 12:
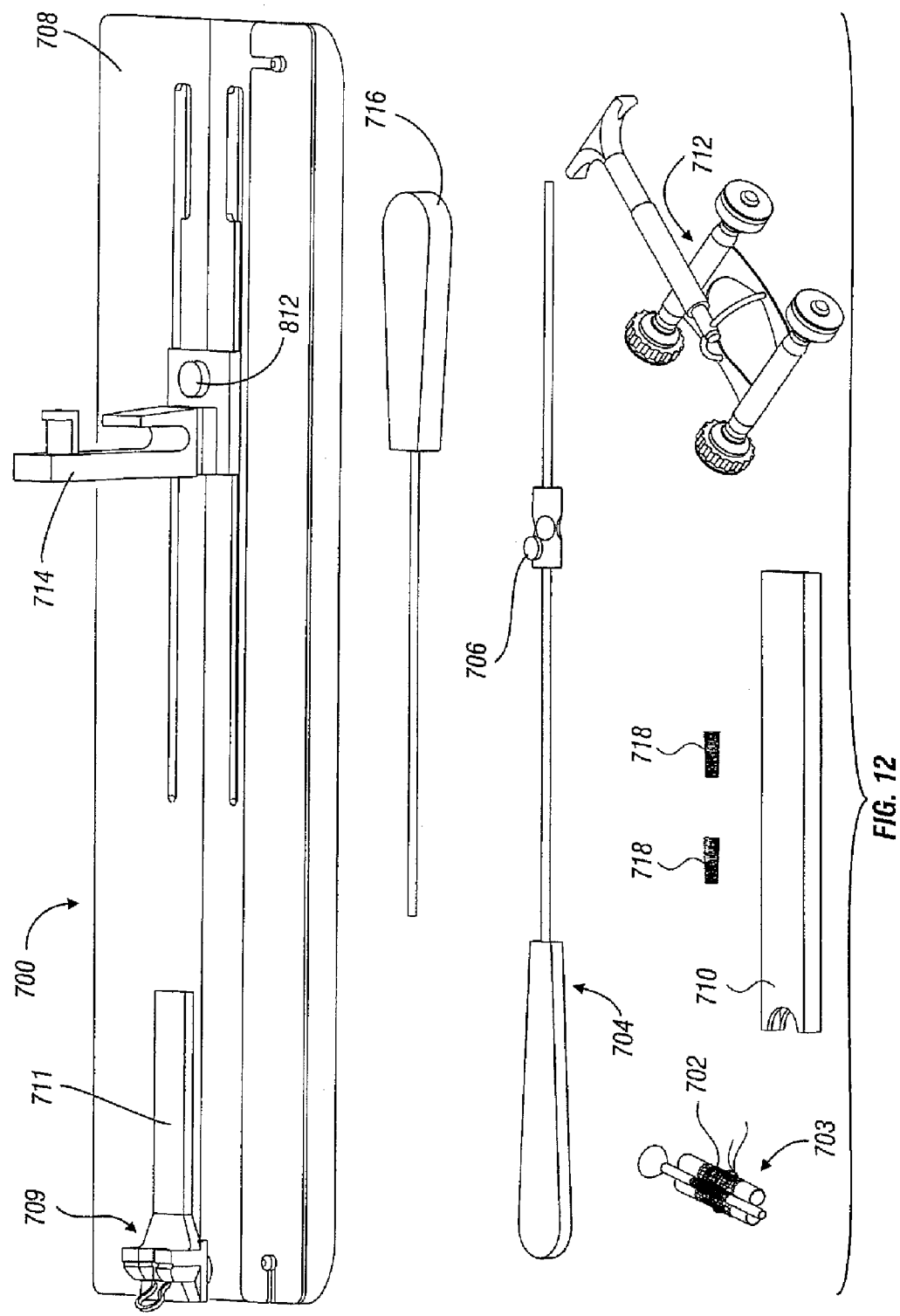
FIG. 12 shows a surgical kit used to implant and fix soft tissue grafts in a bone tunnel using a sheath.

Referring to FIG. 12, a surgical kit 700 used to implant and fix soft tissue grafts in a bone tunnel includes a sheath 702 that is part of a sheath assembly 703, a measurement device 704 with an adjustable stop 706 for measuring the depth of a bone tunnel, a graft positioning board 708 with an ENDOBUTTON™ holder 709 for facilitating coupling of sheath 702 to the grafts and adjusting the position of sheath 702 relative to the grafts, and a tensioning device 712 mounted to a holder 714, which is coupled to board 708. The position of sheath 702 relative to the grafts can be adjusted while the grafts are held in place under tension by tensioning device 712. ENDOBUTTON™ holder 709 includes a scale member 711 and a scale extender element 710 for measuring the length of the grafts to properly position the sheath in accordance with the measured bone tunnel depth.

After insertion of the sheath and the grafts into the bone tunnel, a screw driver 716 is used to insert a screw 718 into the bone tunnel. Screw 718 is preferably tapered to facilitate insertion into sheath 702 and has blunt or rounded screw threads, as opposed to sharp threads, so that the threads do not cut sheath 702 or the soft tissue graft. Two screws 718 are included in kit 700, e.g., a 7×9×30 bone screws (7 mm smaller diameter, 9 mm larger diameter, and 30 mm length) and an 8×10×30 bone screws (8 mm smaller diameter, 10 mm larger diameter and 30 mm length). The operator selects which bone screw to use based upon graft size, tunnel size, and bone quality.

Referring to FIG. 13, sheath 702 includes three contiguous, parallel mesh tubes, 752a, 752b, and 752c. Tubes 752a, 752b, and 752c can be, e.g., integrally woven, braided, knitted, or crocheted from threads. Alternatively, tubes 752a, 752b, and 752c can be separately woven, knitted, or crocheted but otherwise coupled together (e.g., by a suture 758 and/or a sleeve 759, as shown in FIG. 14). Tubes 752a and 752b have a diameter D1 that is large enough to comfortably allow passage of a typical soft tissue graft (e.g., 5 mm). Tubes 752a and 752b need not have the same diameter and may be sized in relation to the diameter of the soft tissue graft designated to pass through each tube. Tube 752c has a diameter D2 large enough to allow passage of a guide wire used to guide a fixation device, e.g., a screw 718, into the bone tunnel (e.g., 2-3 mm).

Sheath 702 has a length L1 in the range of, e.g., approximately one half the length of screw 718 to approximately the length of screw 718 (e.g., 15-30 mm when the screw length is 30 mm). In some implementations, tubes 752a, 752b, and 752c can have different lengths. The walls 754a, 754b, and 754c of tubes 752a, 752b, and 752c, respectively, each have a thickness of, e.g., between 0.1 mm and 1.0 mm.

Sheath 702 can be made from similar materials as described in reference to body 52. The material and configuration of tube 752c provides enough flexibility to allow tube 752c to expand from a first diameter selected for passage of a guide wire (e.g., 2-3 mm) to a second diameter large enough to allow passage of screw 718 (e.g., 9-10 mm).

In another implementation, sheath 702 includes four outer tubes that are circumferentially disposed around a central tube. The four outer tubes are similar in structure to tubes 752a or 752b, and the central tube is similar in structure to tube 752c. In use, four soft tissue grafts are passed through the four outer tubes, and a fixation device is inserted into the central tube.

In yet another implementation, sheath 702 includes a first tube disposed next to a second tube. The first tube is similar in structure to tubes 752a or 752b, and the second tube is similar in structure to tube 752c. In use, a single soft tissue graft is passed through the first tube, and a fixation device is inserted into the second tube.

In yet another implementation, the diameter of tube 752c is equal to the diameter of tubes 752a and/or 752b. The diameter of tube 752c can be slightly larger than the smaller or larger diameter of screw 718 (e.g., 7 mm or 9 mm).

Referring to FIG. 14, sheath assembly 703 includes the sheath 702, three guides 756a, 756b, and 756c, and a securing element, e.g., a suture 758. Guides 756a, 756b, and 756c fit within tubes 752a, 752b, and 752c, respectively. The outer diameter D1 of guides 756a and 756b is slightly less than diameter D1 of tubes 752a and 752b, respectively. Guides 756a and 756b define through channels 753a and 753b, respectively, each having a diameter large enough to allow passage of typical soft tissue grafts (e.g., approx. 5 mm). The length L1 of guides 756a and 756b is, e.g., equal to, or preferably greater than the length L1 of tubes 752a and 752b of sheath 702. Guides 756a and 756b are formed from, e.g., a biocompatible rigid material (e.g., a poly ether-block co-polyamide polymer such as PEBAX™) and thus facilitate insertion of soft tissue grafts into tubes 752a and 752b by preventing tubes 752a and 752b from collapsing or otherwise closing and obstructing graft insertion.

The outer diameter D2 of guide 756c is slightly less than diameter D2 of tube 752c. Guide 756c defines a through channel 753c having a diameter large enough to allow passage of a typical guide wire (e.g., approx. 2-3 mm). Guide 756c preferably has a tunneled end 757 with a diameter D3 that facilitates insertion of the guide wire into tube 752c. Guide 756c has a length L2, which is longer than that of the sheath and guides 756a and 756b. Guide 756c is formed from a biocompatible rigid material that is the same as or different than that of guides 756a and 756b.

Once the grafts are coupled to sheath 702, and sheath 702 is properly positioned relative to the grafts in accordance with the measured bone tunnel depth, as described further below, suture 758 is used to fix sheath 702 in position. The tie suture is, e.g., woven into, braided, or otherwise coupled to flexible mesh tubes 752a, 752b, and/or 752c.

Referring to FIGS. 12, 15A and 15B, measurement device 704 includes a handle 705, a rod 707 extending from handle 705, and an adjustable stop 706 having a cylindrical body 760 defining a cylindrical channel 762 for slidably receiving rod 707. Body 760 defines a groove 765 at an end 766 of channel 762 in which an o-ring 764 is positioned to ensure a snug fit. Body 760 also defines a radial, threaded hole 770 into which a thumb screw 767 with an engaging end 768 is inserted. Thumb screw 766 is fixed in place by a set screw 772 inserted in a hole 774 defined by a wall 776 of cylindrical body 760.

Figure 16:
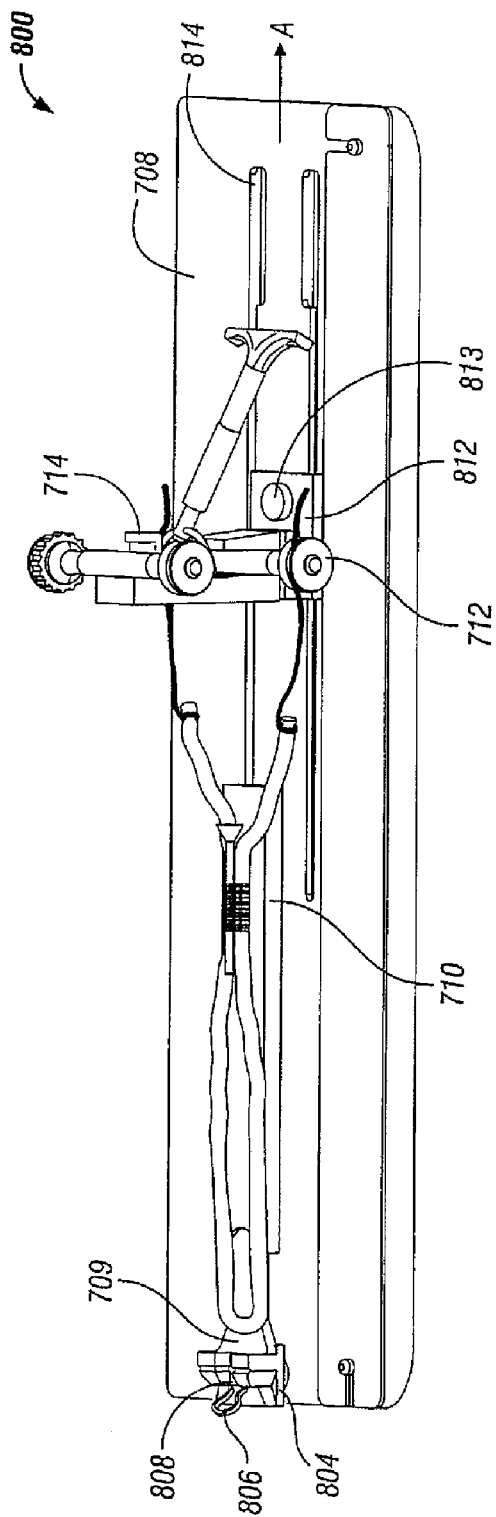
FIG. 16 is a perspective view of a graft measurement and sheath positioning assembly of the kit of FIG. 12.
Figure 16:
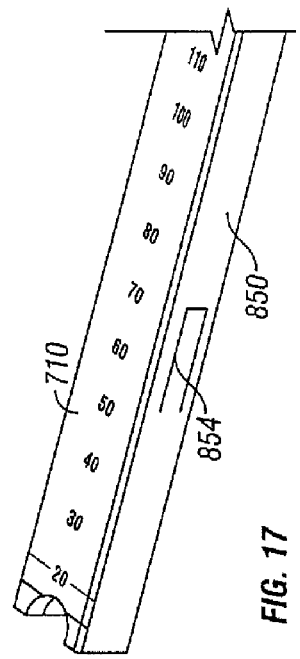

Referring to FIG. 16, a graft measurement and sheath positioning assembly 800 of kit 700 includes the graft positioning board 708 with attached ENDOBUTTON™ holder 709 and scale extender element 710, tensioning device holder 714, and tensioning device 712 mounted to holder 714.

Figure 17:
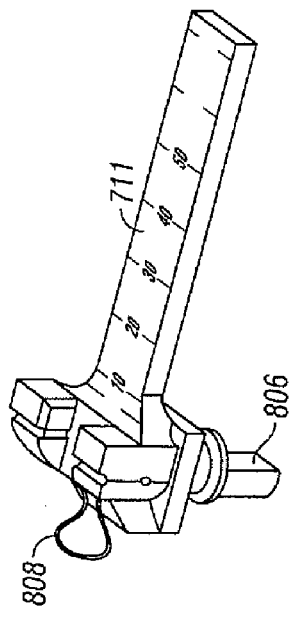
FIG. 17 shows a scale extender element and ENDOBUTTON™ holder of the kit of FIG. 12.

Referring also to FIG. 17, scale member 711 of ENDOBUTTON™ holder 709 includes, and an ENDOBUTTON™ coupler 808 and a pin 806 for attaching ENDOBUTTON™ 709 to board 708. Scale extender element 710 includes a rectangular housing 850 defining a hollow cavity 852 sized and shaped to receive scale member 711 of ENDOBUTTON™ holder 709. Housing 850 includes arms 854 that normally protrude into the interior of the housing and are pushed outwards by scale member 711. The frictional engagement of 711 against arms 854 secures scale member 711 within scale extender element 710. Soft tissue grafts of a typical length (e.g., 120 mm), which otherwise would extend beyond the length of scale member 711 of the ENDOBUTTON™ holder 709 (e.g., 70 mm), are positioned on and mechanically supported by the scale extender element 710.

Referring again to FIG. 16, tensioning device holder 714 is coupled to board 708 by a coupler 812 that rides in a guide rail 814 defined in board 708. Tensioning device holder 714 is movable in the direction of arrow A along guide rails 814 to place grafts coupled to loop 804 under tension, and can be fixed in place using a screw 813 of coupler 812.

Figure 18:
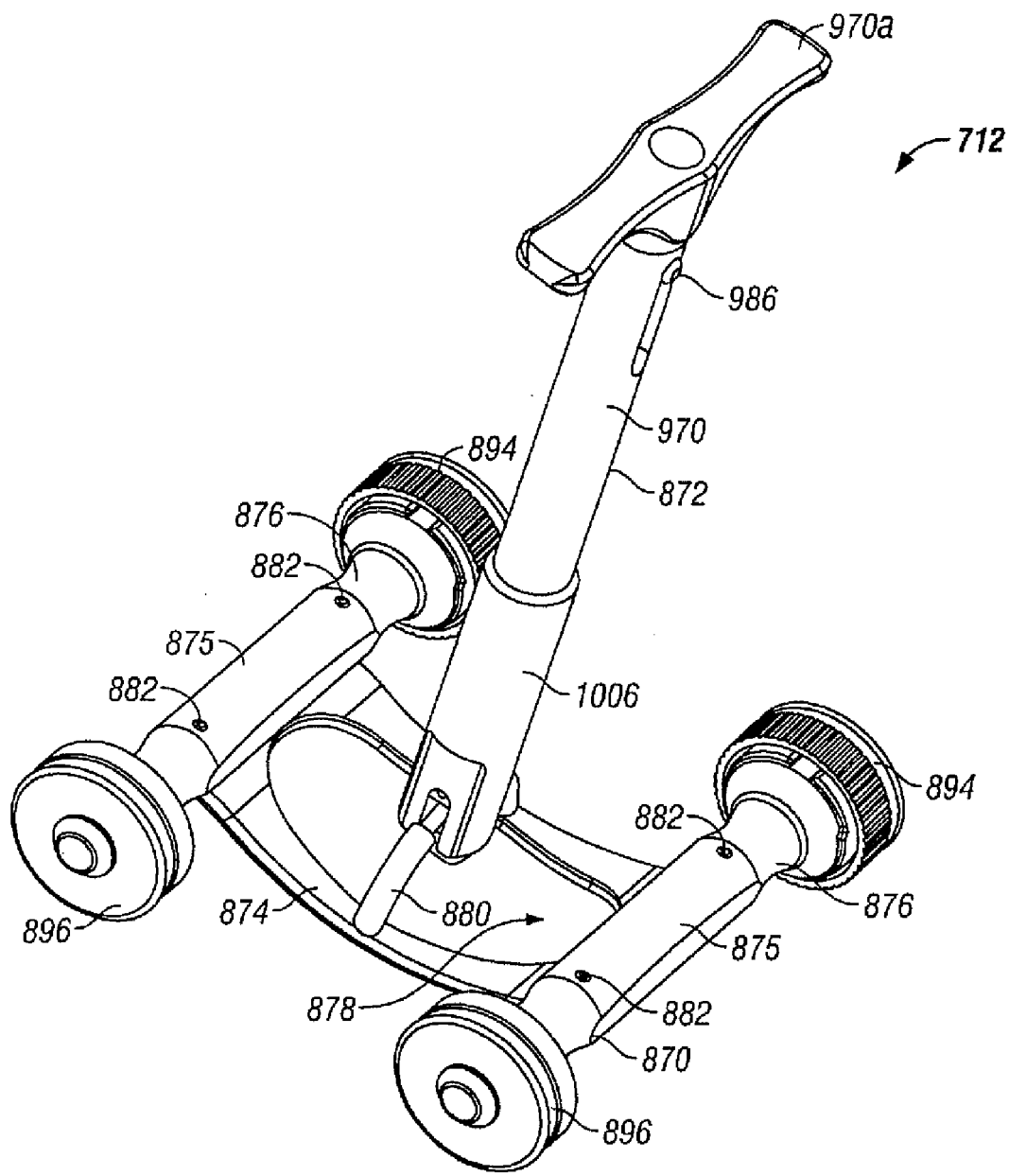
FIG. 18 is a perspective view of a tensioning device of the kit of FIG. 12 including a tie rod assembly and a handle.

Referring to FIG. 18, the tensioning device 712 includes a tie rod assembly 870 coupled to a handle assembly 872. Tie rod assembly 870 includes a frame 874 that connects two parallel rod assemblies 876. Frame 874 defines a hole 878 bisected by an arch 880. Frame 874 includes two parallel hollow tubes 875 that receive rod assemblies 876, which are attached to tubes 875 by pins 882.

Figure 19:
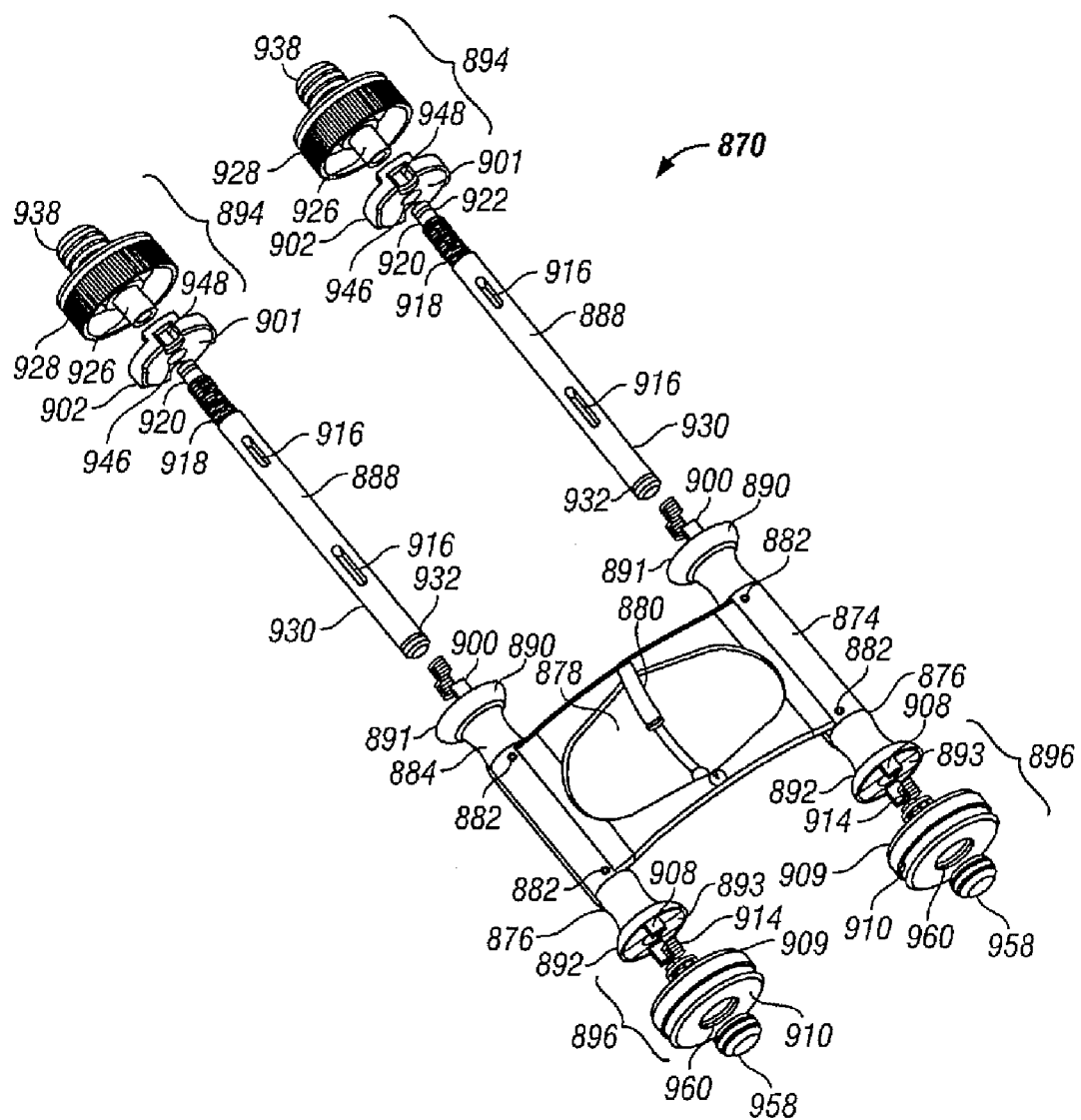
FIG. 19 is an exploded view of the tie rod assembly of FIG. 18.
Figure 20:
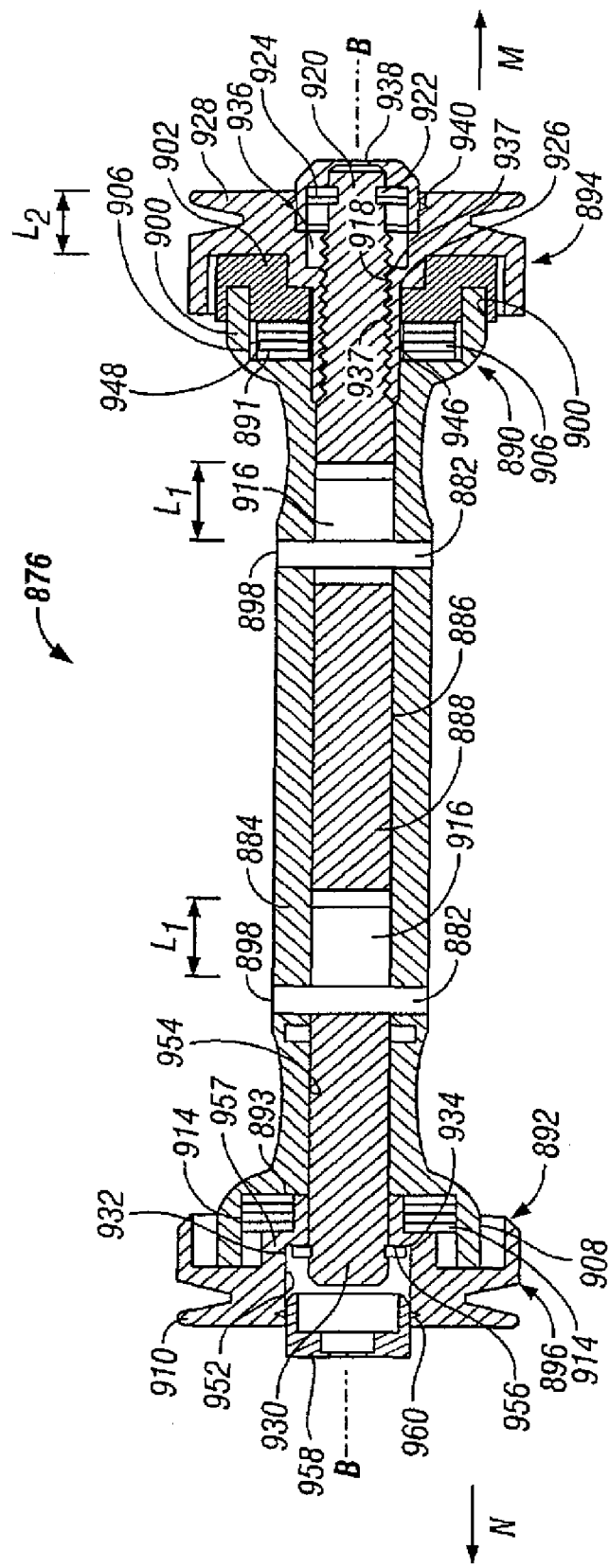
FIG. 20 is a cross-sectional view of a rod assembly of the tie rod assembly of FIG. 19.

Referring to FIGS. 19 and 20, each rod assembly 876 includes a rod housing 884 that defines a cylindrical channel 886 sized and shaped to receive a rod 888, which is slidable within channel 886 relative to rod housing 884. Rod housing 884 also defines bore holes 898 configured to receive pins 882.

Rod 888 defines two slots 916 through which pins 882 pass. The slots 916 limit axial movement of the rod 888 relative to rod housing 884 along axis B to a maximum displacement distance L1 approximately equal to the width of the slots minus the diameter of pins 882. At one end, rod 888 includes a threaded segment 918 and an end segment 920 defining a groove 922 that accepts a retaining ring 924. At the other end, rod 888 has a rod end 930 defining a groove 932 that accepts a retaining ring 934.

Rod housing 884 includes a first mating end 890 and a second mating end 892. First mating end 890 is coupled to a knurled knob assembly 894, and second mating end 892 is coupled to a knob assembly 896. First mating end 890 includes a mating surface 891 and alignment posts 900. Second mating end 892 includes a mating surface 893 and alignment posts 908. Knurled knob assembly 894 includes a mating plate 902 having a mating surface 901, which mates with surface 891 of end 890, and a knurled knob 928 having a threaded post 926 into which threaded segment 918 of rod 888 is screwed. Knob assembly 896 includes a knob 910 having a mating surface 909, which mates with surface 893 of end 892, and a non-threaded post 9576 defining a bore 954 that receives rod end 930.

Figure 20A:
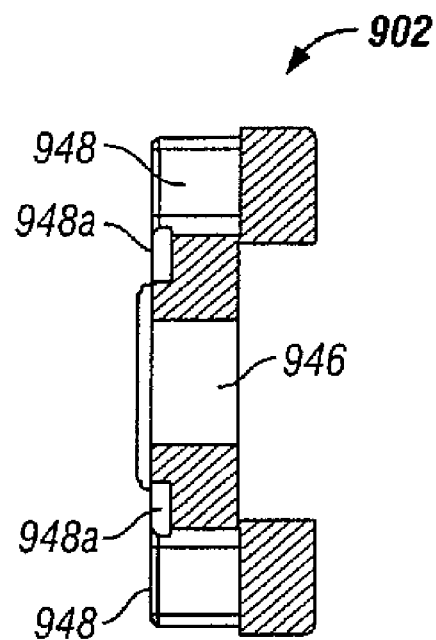
FIG. 20A is a cross-sectional view of a mating plate of the rod assembly.

Knurled knob 928 has a base 937 defining a cavity 936 partially bounded by a threaded portion 940 that receives a threaded end plug 938. Threaded segment 918 of rod 888 extends through post 926 and into cavity 936. Mating plate 902 is positioned between first mating end 890 and knurled knob 928. Referring to FIG. 20A, mating plate 902 defines a bore hole 946 through which post 926 passes, and two recesses 948 that each accept an alignment post 900 and two recesses 948a that each accept a spring 906. Alignment posts 900 limits any rotation between mating plate 902 and mating end 890, and springs 906 are compression springs, which acts between mating surfaces 891 and 901.

Figure 20B:
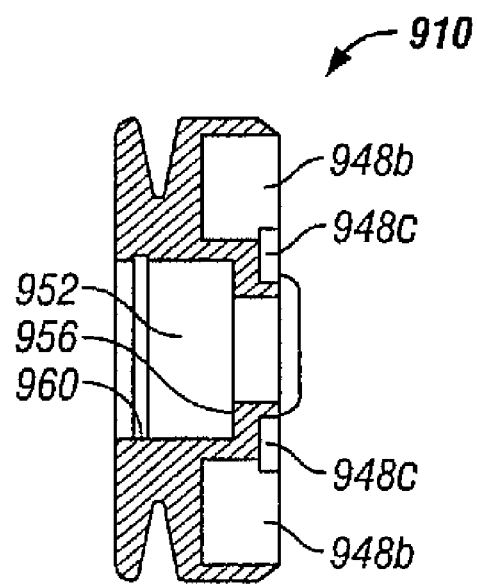
FIG. 20B is a cross-sectional view of a knob of the rod assembly.

Knob 910 has a base 956 defining a cavity 952 partially bounded by a threaded portion 960 that receives a plug 958. Referring to FIG. 20B, knob 910 defines two recesses 948b that each accept an alignment post 908 and two additional recesses 948c that each accept a spring 914. Alignment posts 908 limits any rotation between knob 910 and mating end 892, and springs 914 are compression springs, which acts between mating surfaces 893 and 909.

With knurled knob 928 fully screwed onto threaded segment 918 of rod 888, rod 888 is fixed in place with the respective mating surfaces engaged. When knurled knob 928 is loosened, rod 888 can move along axis B with slots 916 sliding along pins 882. Springs 906, 914 act to center rod 888 between the knob assemblies 894, 896, and retaining rings 924, 934 hold knobs 928, 910 onto the knob assemblies by contacting bases 937, 956, respectively. In use, turning knob 928 loosens both knobs such that suture or other material to be retained can be positioned between the mating surfaces of both knobs. Tightening knob 928 in turn tightens both knobs to secure the suture in place. Both sutures are thus secured, one to each end of a rod assembly 876 of tie rod assembly 870, at substantially the same time through the turning of a single knob (i.e., the knurled knob). Securing the sutures simultaneously and with only one knob decreases the number of "hands" involved in this surgical step.

While the implementation of the tie rod assembly 870 shown in FIGS. 18-20 has two parallel rod assemblies 876, other implementations can have only one rod assembly 876 or more than two rod assemblies 876, depending upon the number of strands of soft tissue to be implanted in the bone tunnel.

Figure 21:
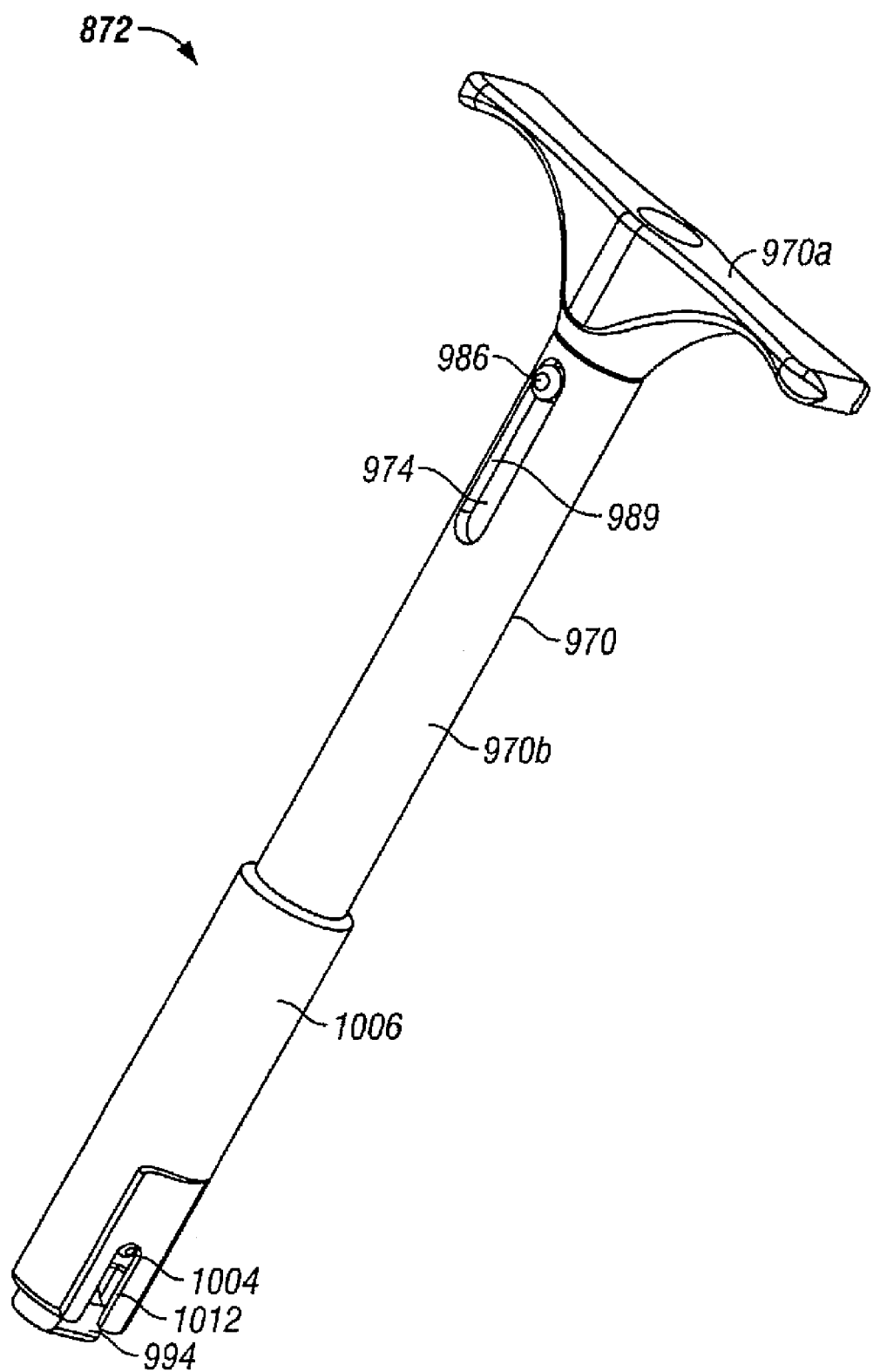
FIG. 21 is a perspective view of the handle of FIG. 18.

Referring to FIG. 21, handle assembly 872 includes a handle section 970, a sleeve 1006, and an inner shaft assembly 974 coupling handle section 970 to sleeve 1006. Handle section 970 defines a slot 989 and inner shaft assembly 974 has a pin 986 that slides within slot 989 such that handle section 970 can be moved relative to inner shaft assembly 974. Sleeve 1006 defines a slot 1012 and inner shaft assembly 974 has a pin 1004 that slides within slot 1012 such that sleeve 1006 can be moved relative to inner shaft assembly 974. Handle section 970 has a handle 970a and a tubular extension 970b.

Figure 22:
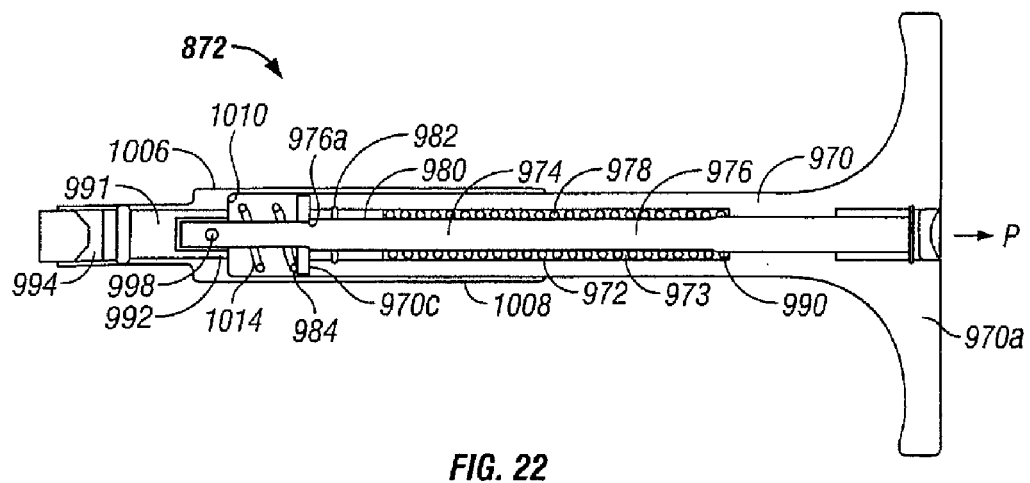
FIG. 22 is a cross-sectional view of the handle of FIG. 21.

Referring to FIG. 22, handle section 970 defines a through bore 972 sized and shaped to receive inner shaft assembly 974. Sleeve 1006 defines a through bore 1008 for receiving handle tubular extension 970b and inner shaft assembly 974. Inner shaft assembly 974 includes a shaft 976 and an end piece 991 coupled to shaft 976 by a pin 998. Bore 972 has an enlarged region 973 in which is positioned a spring 978 surrounding shaft 976. Spring 978 is positioned on shaft 976 between a shelf 990 of shaft 976 and a bushing 980. Bushing 980 is positioned next to a retaining ring 982 which is attached to handle 970 and slidable relative to inner shaft assembly 974. Positioned within sleeve 1008 and abutting a distal end 970c of handle section 970 and a shelf 976a of shaft 976 is a washer 984. Also positioned within sleeve 1008 between washer 984 and a shelf 1010 of sleeve 1006 is a second spring 1014.

Figure 23:
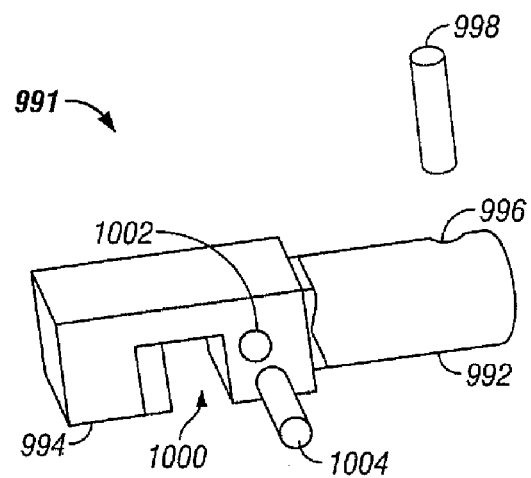
FIG. 23 shows an end piece of an inner shaft assembly of the handle of FIG. 21.

Referring to FIG. 23, end piece 991 includes a cylindrical member 992 and a coupler 994. Cylindrical member 992 defines a bore hole 996 for receiving pin 998 to couple cylindrical member 992 to shaft 976. Coupler 994 defines a slot 1000 for coupling handle assembly 872 to arch 880, and a bore hole 1002 that receives a pin 1004.

The handle assembly 872 is attached to the tie rod assembly 870 by pulling sleeve 1006 in the direction of arrow P relative to the handle 970. Pulling sleeve 1006 compresses spring 1014 and exposes coupling slot 1000 of coupler 994. Arch 880 of tie rod assembly 870 is then inserted into coupling slot 1000. Once arch 880 is inserted into slot 1000, the pulling force is removed and spring 1014 automatically retracts the coupler 994 back into the sleeve 1006. Pin 1004 keeps sleeve 1006 from sliding distally off handle 970 and inner shaft assembly 974.

Movement of handle 970 relative to inner shaft assembly 974 against the force of spring 978 provides an indication of tension applied to handle 970 when handle assembly 872 is coupled to tie rod assembly 870. This relative movement causes pin 986 to slide along slot 989. Slot 989 is marked accordingly to relate the movement of pin 986 to a tensile load (e.g., 1-100 Newtons). When a tensile load is imparted to tie rod assembly 870 via coupler 994, spring 978 is compressed between retaining ring 982 attached to handle 970 and shelf 990 of inner shaft 976. Compression of spring 978 results in movement of handle 970 relative to inner shaft 976 and, thereby results in movement of tension indicator pin 986 (attached to shaft 976) relative to slot 989 (defined by handle 970). A greater tensile load results in a greater compression of spring 978, a correspondingly greater displacement of tension indicator pin 986 relative to slot 989, and therefore, a greater measurement of tension.

Figure 24:
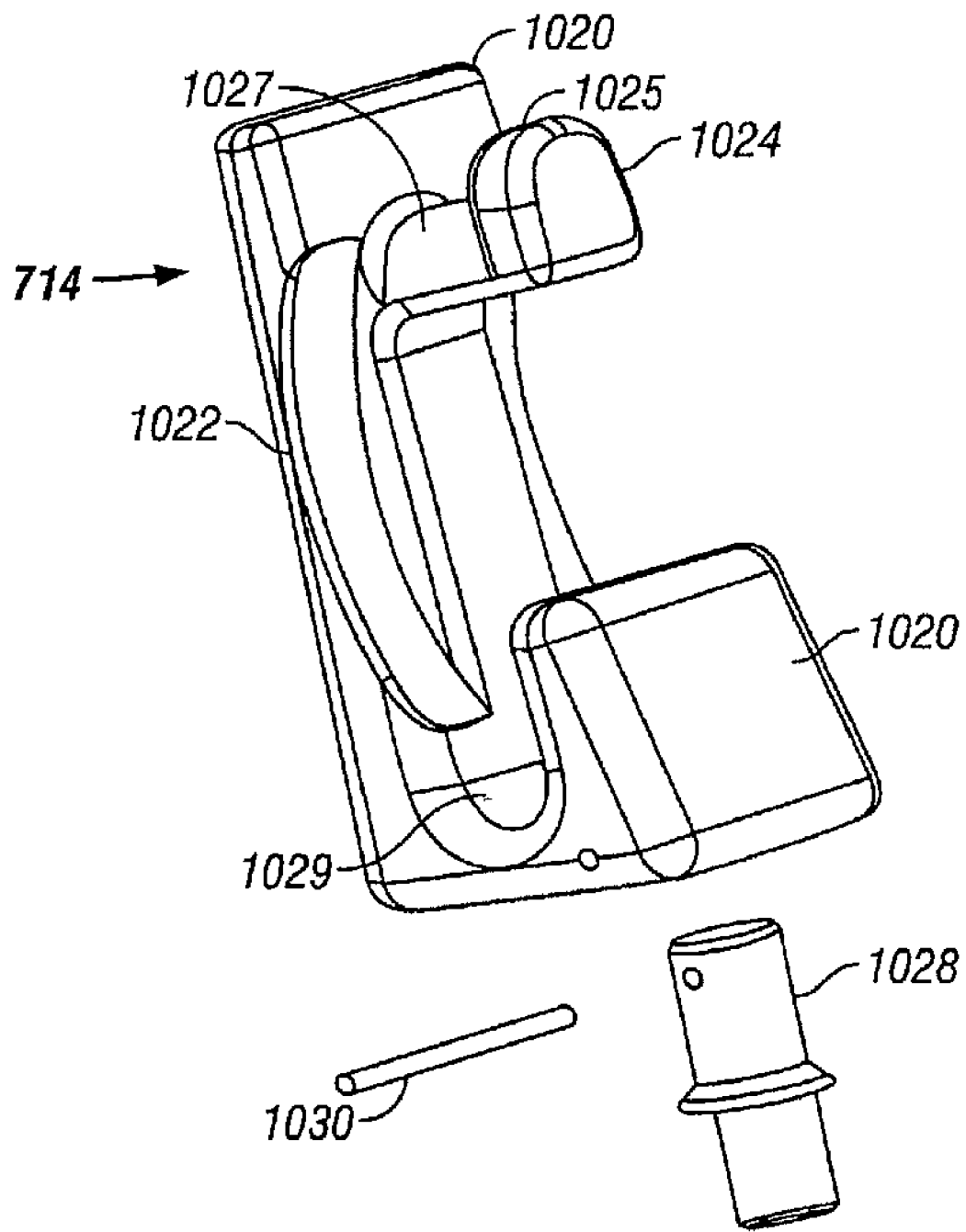
FIG. 24 is a perspective view of a tensioning device holder of the kit of FIG. 12.

Referring to FIGS. 16 and 24, tensioning device 712 is attached to board 708 using device holder 714 and coupler 812. Tensioning device holder 714 includes a body 1020 with a vertical member 1022 from which extends a small arm 1024 and a base arm 1026. Small arm 1024 has a lip 1025 sized and shaped to fit within hole 878 of frame 874 (FIG. 18) such that one of the rod assemblies 876 can be positioned on a surface 1027 of arm 1024. Base arm 1026 defines a groove 1029 in which the other rod assembly 876 is positioned. Device holder 714 includes a plug 1028 attached to base arm 1026 by a pin 1030. Tensioning device holder 714 is attached to board 708 by inserting plug 1028 into coupler 812.

Figure 25:
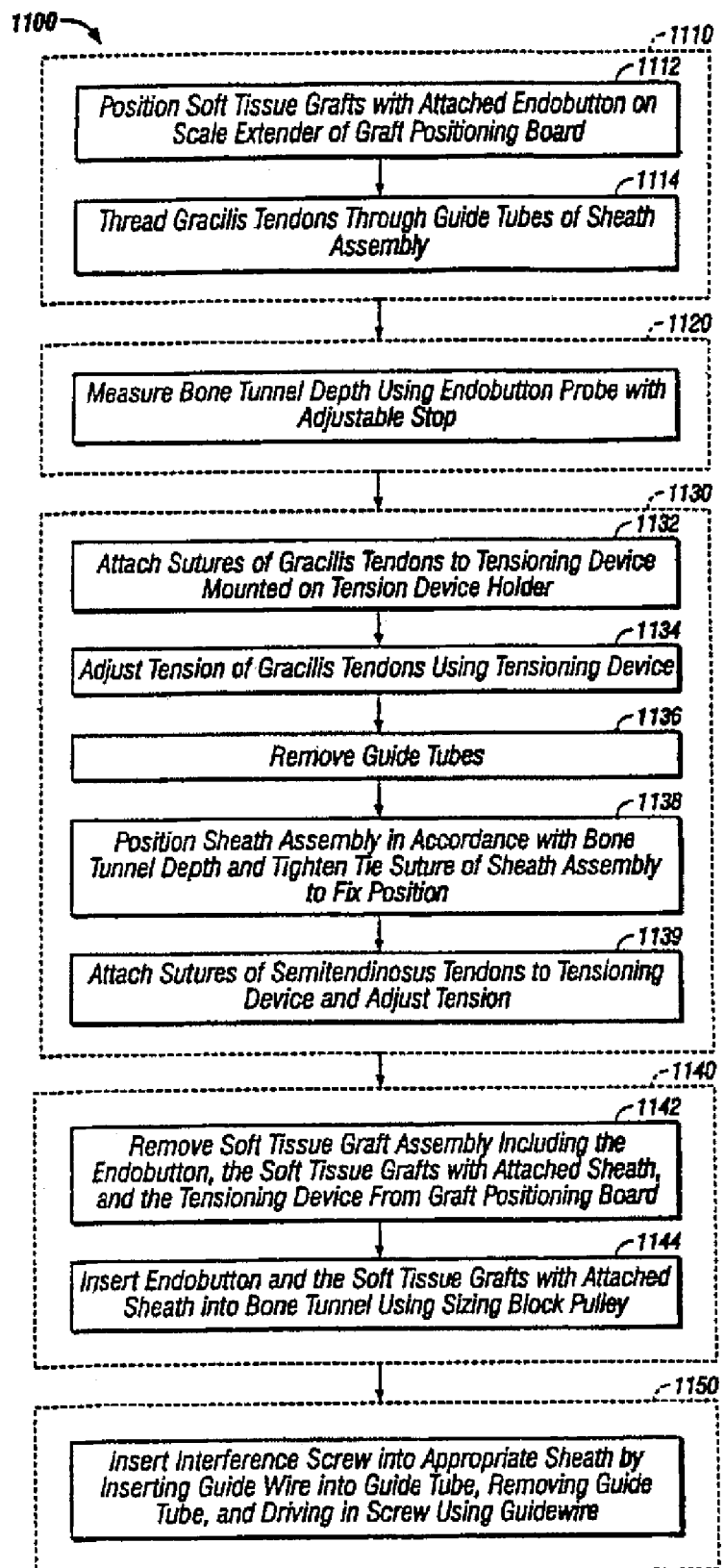
FIG. 25 is a detailed flow chart of a surgical process to implant and fix soft tissue grafts in a bone tunnel using a sheath.

FIG. 25 shows a detailed flow diagram of a specific implementation 1100 of surgical process 600 using kit 700 directed to ACL repair. Operations 1110, 1120, 1130, 1140, and 1150 correspond to operations 610, 620, 630, 640, and 650, respectively.

Figure 26A:
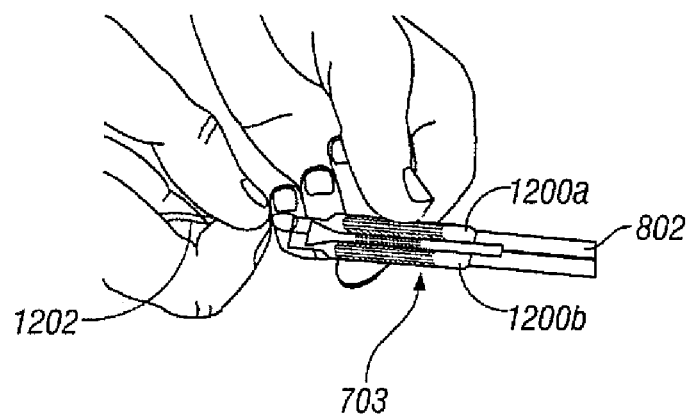
FIGS. 26A and 26B illustrate the threading of tendons through the sheath assembly of FIG. 14.
Figure 26B:
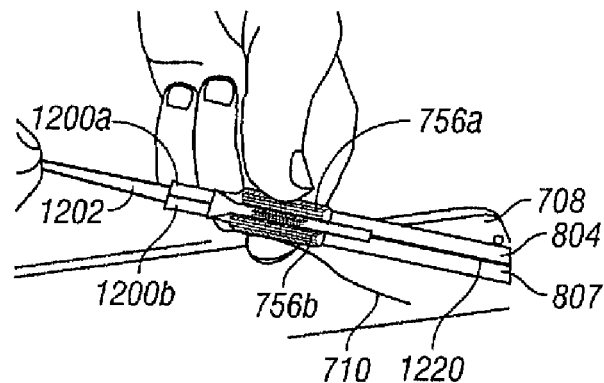

Referring also to FIGS. 26A and 26B, initially, harvested semitendinosus and gracilis tendons 802 are sutured, folded, and inserted through a suture loop 1221 that couples the tendons to an ENDOBUTTON™ 1220. The operator attaches ENDOBUTTON™ 1220 to ENDOBUTTON™ loop 804, and places the tendons on scale extender 710 of graft positioning board 708 (1112). The operator then threads the gracilis tendon ends 1200a, 1200b through guide tubes 756a and 756b of sheath assembly 703 (1114) using attached sutures 1202.

The operator measures the depth of the tibial and femur tunnels using measurement device 704 (1120). The depth of the bone tunnels is measured by inserting rod 707 of measurement device 704 into the bone tunnels until the distal end of the cylindrical probe rod reaches the end of the bone tunnels. The operator then advances adjustable stop 706 up to the bone tunnel entrance by sliding stop 706 along rod 707, and secures adjustable stop 706 in position using thumb screw 766. Rod 707 is then removed from the bone tunnels, and the distance between stop 706 and the distal end of the rod corresponds to the bone tunnel depth. This depth measurement can be done at any time prior to operation 1138 (i.e., prior to adjusting the position of the sheath 703 and fixing it in position).

Figure 27:
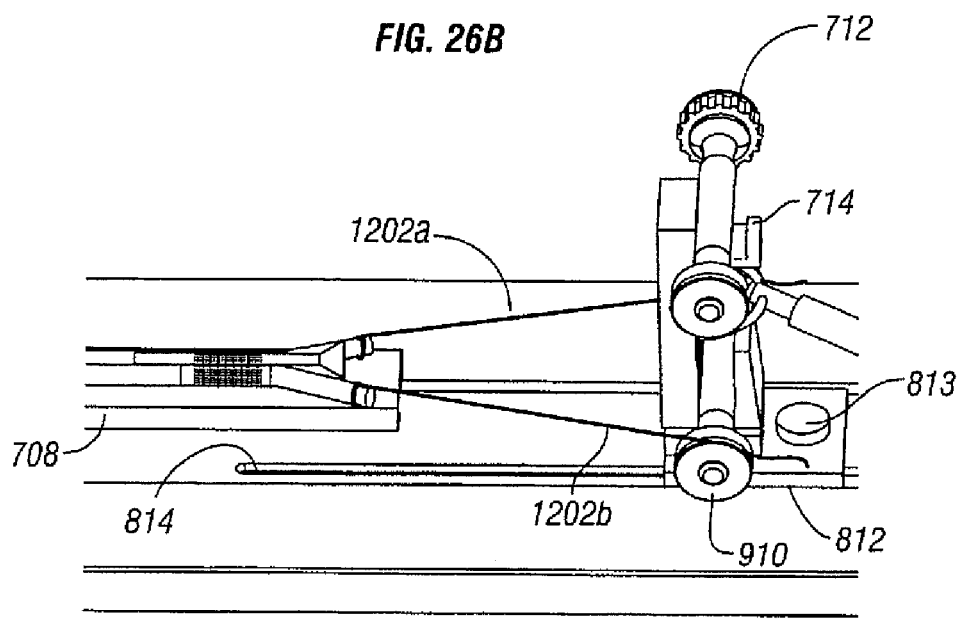
FIG. 27 illustrates the securing of two graft ends to the tensioning device of FIG. 18.

Referring to FIG. 27, the operator couples sutures 1202 attached to tendon ends (e.g., gracilis tendon ends) 1200a, 1200b to tensioning device 712 mounted on tensioning device holder 714 (1132). Tensioning device holder 714 is fixed in any position along guide rail 814 that provides a distance between the tensioning device 712 and the sheath 702 that conveniently allows subsequent insertion of tapered screw 718 into the bone tunnel. First knurled knob 928 is loosened, and one suture 1202a is positioned between knurled knob 928 and mating plate 902, and a second suture 202b is positioned between knob 910 and mating surface 893 (FIG. 19). Once both sutures are in position, the operator uses one hand to pull both sutures to the point where there is no slack in the sutures and the other hand to tighten knurled knob 928 to secure both sutures to tensioning device 712.

Figure 28:
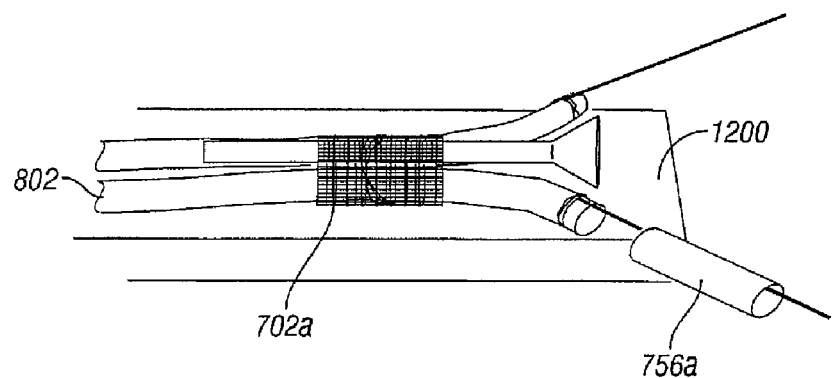
FIG. 28 illustrates the removal of the guides from the sheath assembly.
Figure 29:
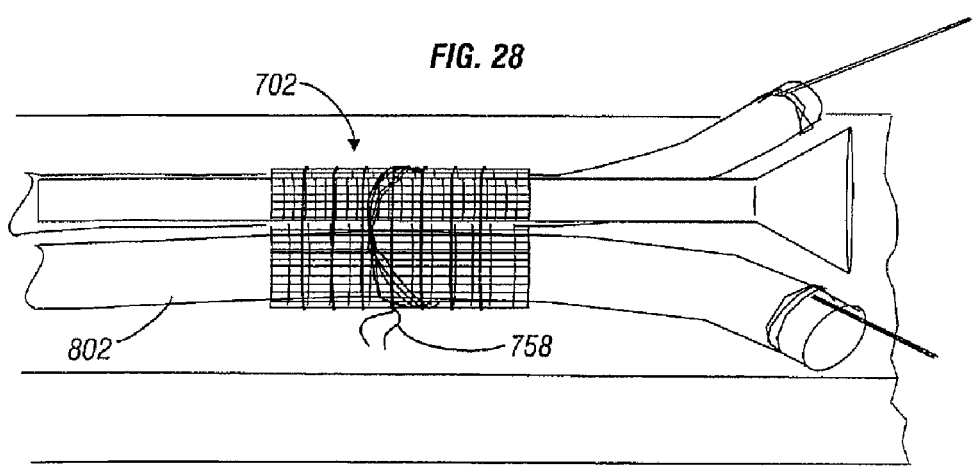
FIG. 29 illustrates the fixing of the sheath assembly to an additional graft using the suture.

Referring to FIG. 28, the operator then positions sheath 702 relative to grafts 802 such that the distance between ENDOBUTTON™ loop 804 and the proximal end 702a of sheath 702 corresponds to the measured bone tunnel depth (1138). The guide tubes 756a and 756b are then removed from grafts 802, and tie suture 758 is used to fix sheath 702 in place relative to grafts 802 (FIG. 29).

Figure 30:
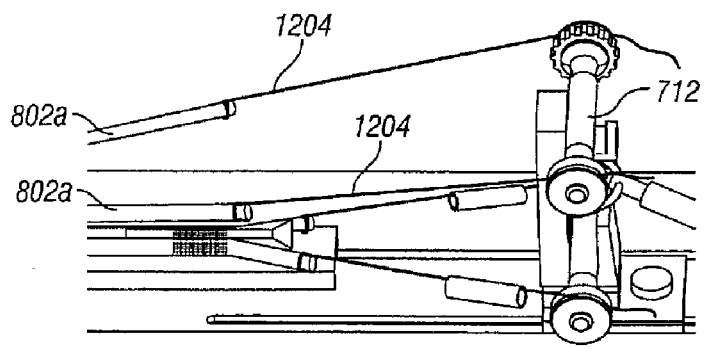
FIG. 30 illustrates the securing of two additional graft ends to the tensioning device.

Referring to FIG. 30, the operator then couples sutures 1204 attached to the two ends of the semitendinosus tendon 802a to the tensioning device 712 as discussed above with reference to FIG. 27.

Figure 31A:
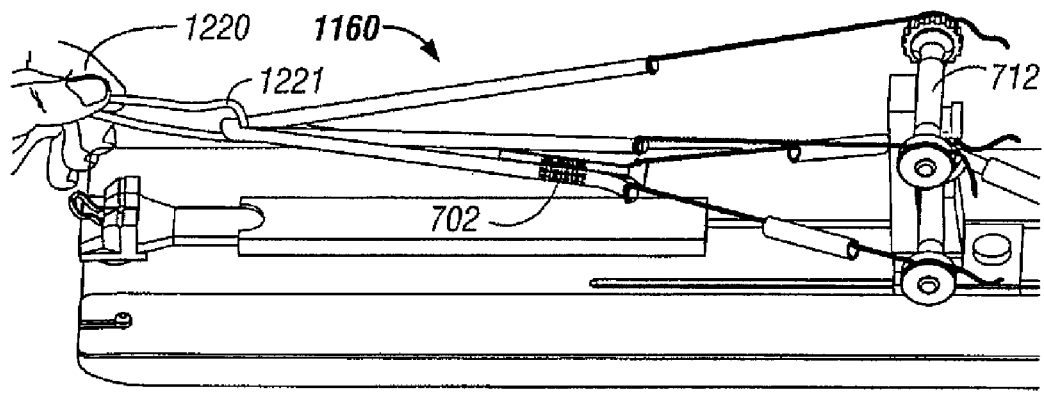
FIGS. 31A and 31B illustrate the tensioning of the grafts.
Figure 31B:
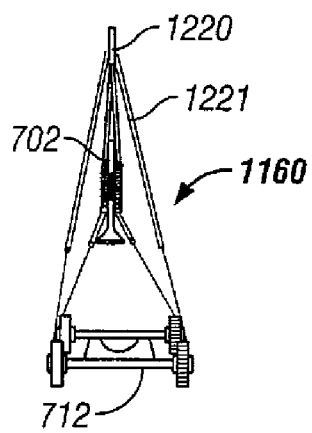
Figure 32:
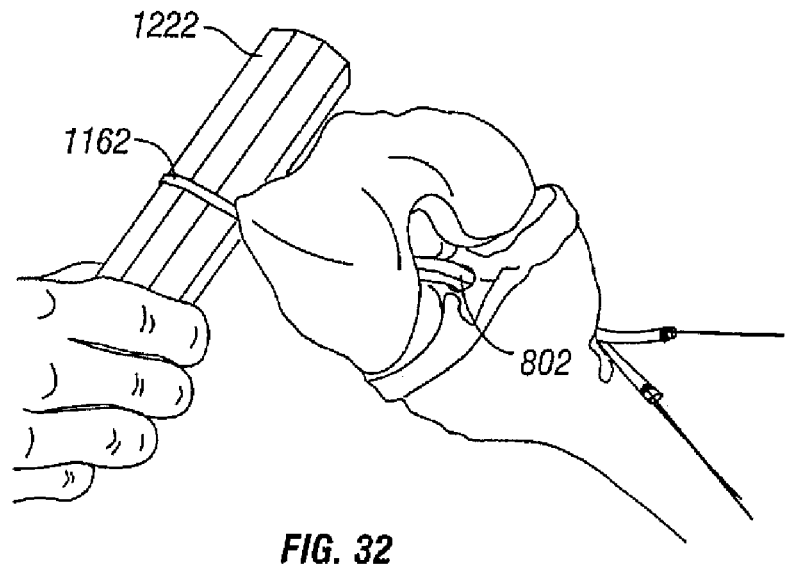
FIGS. 32-33B illustrate the positioning of the sheath assembly and grafts within a knee joint.

Referring to FIGS. 31A and 31B, the operator removes the soft tissue graft assembly 1160, which includes ENDOBUTTON™ 1220, the tendons, sheath 702, and tensioning device 712, from graft positioning board 708 (1142), and attaches one or more sutures 1222 to ENDOBUTTON™ 1220(FIG. 32). The operator then inserts sutures 1222 and ENDOBUTTON™ 1220 into the tibial tunnel and pulls on sutures 1222 using a block 1162 to position the tendons within the bone tunnels (1144). Block 1162 provides a mechanical advantage that facilitates pulling the ENDOBUTTON™ loop, the tendons and the sheath 702 through the bone tunnels.

Figure 33A:
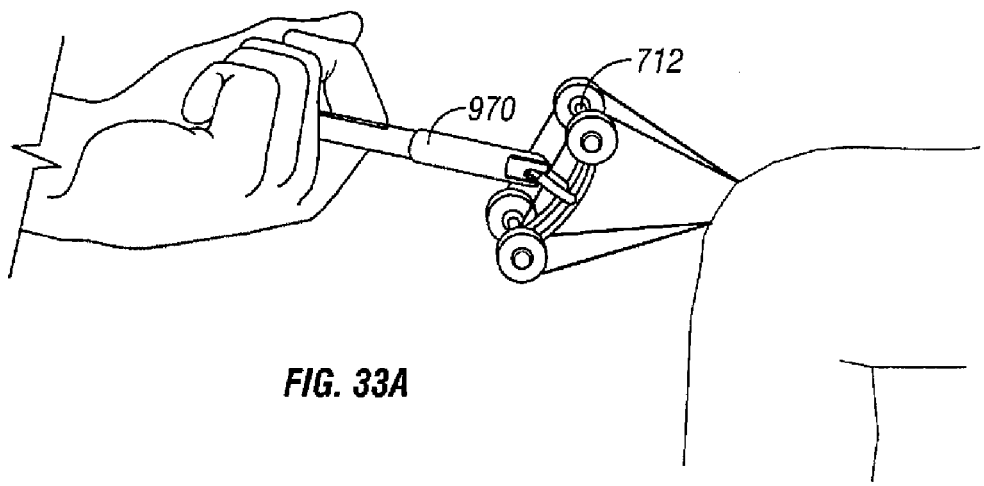
Figure 33B:
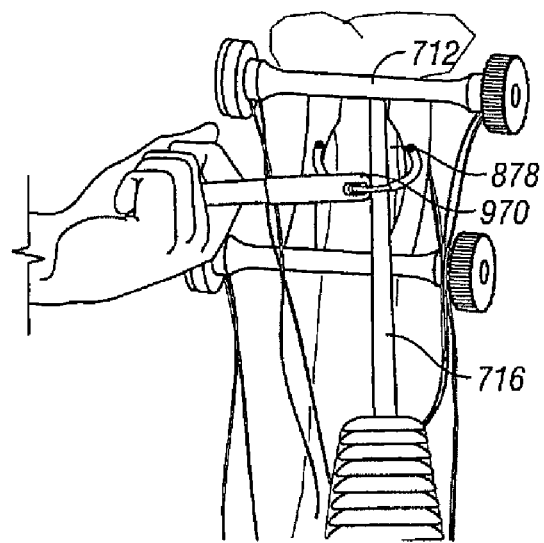

Referring to FIGS. 33A and 33B, once sheath 702 is pulled into position such that end 702a of sheath 702 is flush with the entrance to the tibial bone tunnel, the operator inserts a guide wire (not shown) into funneled end 757 of guide wire tube 756c, removes guide wire tube 756c by sliding the guide wire tube out of tube 752c of sheath 702 and over the guide wire, and then advances a tapered interference screw 718 over the guide wire and into tube 752c using screw driver 716 (1150). During advancement of the screw, the operator maintains the desired tension on the tendons by pulling on handle assembly 970 while monitoring the position of the tension indicator pin 986 in slot 989. Use of the tensioning device during screw advancement provides the advantage of equalizing the tension of the tendons and organizing the tendons to facilitate accurate positioning of the interference screw 718 in tube 752c of sheath 702. Driver 716 is conveniently inserted through hole 878 of the tensioning device.

Figure 34:
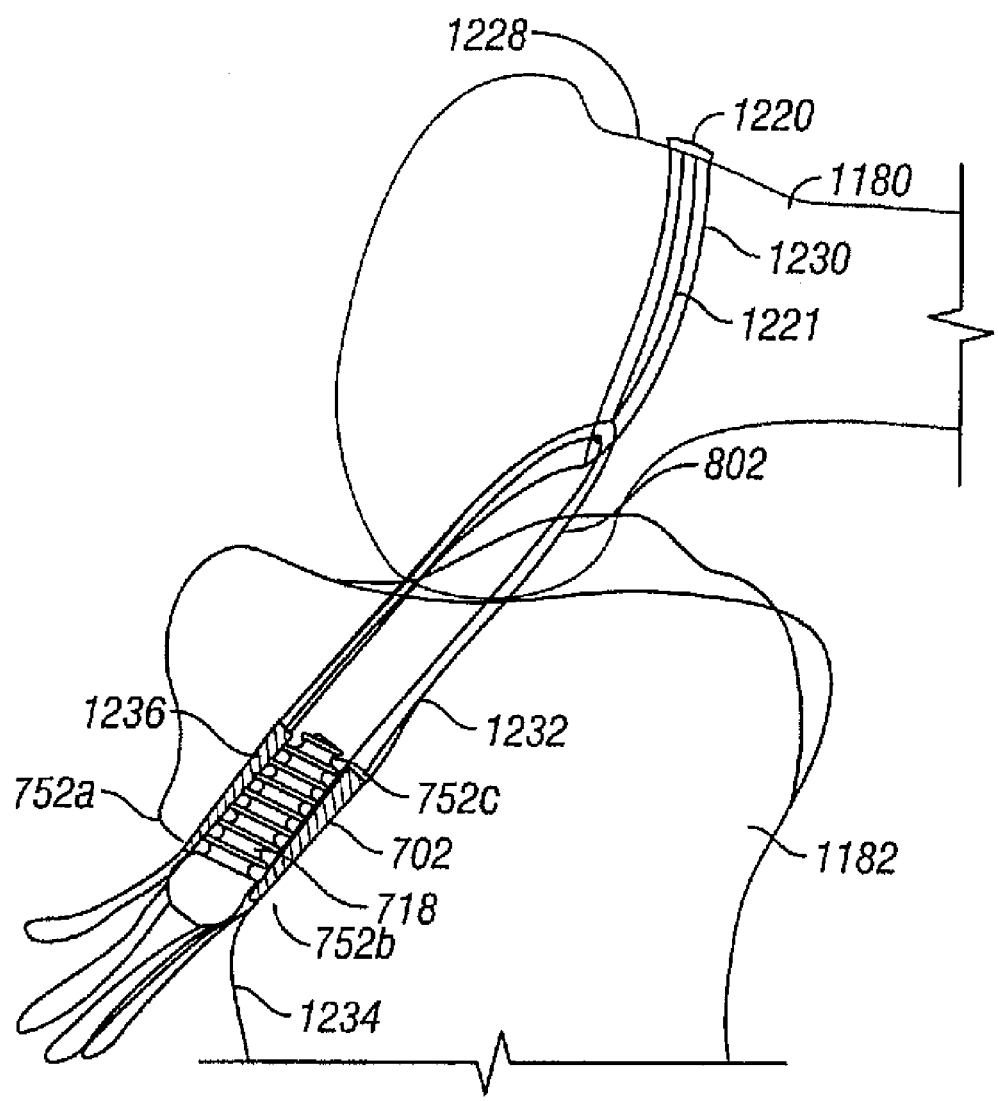
FIG. 34 is a cross-sectional view showing the sheath assembly and grafts fixed in position within the bone tunnel in the tibia.

Referring to FIG. 34, when in position, ENDOBUTTON™ 1220 is on the surface 1228 of femur 1180, suture loop 1221 extends into the femur tunnel 1230, grafts 802 extend from suture loop 1221 in the femur tunnel to the tunnel 1232 in tibia 1182, and sheath 702 with interference screw 718 are flush with the surface 1234 of the tibia. The gracilis tendon grafts and their surrounding tubes 752a and 752b as well as the semitendinosus tendons are compressed between screw 718 (located in tube 752c) and the wall 1236 of the bone tunnel 1232 to fix the grafts within the bone tunnel.

The sheaths need not be used exclusively with bone screws. The sheaths can be used to improve fixation of other types of implantable fixation devices, such as soft tissue tacks, plugs, and suture anchors. The size and shapes of the sheaths can be varied to accommodate the different types of fixation devices. The sheaths need not be used in bone tunnels. For example, soft tissue can be positioned inside a sheath, and the sheath attached to the side of a bone with a fixation device such as a tack.

Knurled knob 928 need not be knurled. Knob 928 can instead have a different type of grippable surface that allows application of a torsional load without slipping (e.g., a scalloped or octagonal surface).

Tensioning device 712, scale extender element 710, and adjustable stop 706 need not be used solely for soft tissue grafts but can instead be used for bone-tendon-bone grafts.

The displacement of sleeve 1008 relative to handle 970 can be used to indicate tension by adding scale markings to handle 970. The sliding of handle 970 relative to sleeve 1008 provides an indication similar to that provided by the sliding of pin 986 in slot 989. The relative movement causes the scale markings on handle 970 to be exposed and to indicate the applied tension.

The process 1100 can be used for achilles tendons, fascia lata, or other harvested tendons. The ENDOBUTTON™ or ENDOBUTTON™ loop of process 1100 may be replaced by an additional bone screw, a suture through a washer, a suture button, or a post.

What is claimed is:

1. A soft tissue fixation assembly comprising a medical sheath and a fixation device, said medical sheath for organizing soft tissue and comprising:
a first mesh tube including a flexible body, wherein the first mesh tube is sized and shaped to conform to the shape of a shaft of said fixation device when the fixation device is received therein;
at least one second mesh tube substantially parallel and interconnected to the first mesh tube such that the first mesh tube and the at least one second mesh tube are coupled together substantially along their lengths, the second tube including a flexible body; and a flexible mesh sleeve configured to be inserted into a bone tunnel, wherein the lengths of the first mesh tube and the second mesh tube are positioned within the flexible mesh sleeve.

2. The sheath of claim 1, further comprising a third mesh tube coupled to the first mesh tube, the third mesh tube including a flexible body sized and shaped to receive a soft tissue graft.

3. The sheath of claim 2, wherein the first mesh tube has a different diameter than the second and third mesh tubes.

4. The sheath of claim 3, wherein the second and third mesh tubes have the same diameter.

5. The sheath of claim 2, wherein the second and third mesh tubes have the same diameter.

6. The sheath of claim 1, wherein at least one of the first mesh tube and the second mesh tube comprise a biocompatible material selected from the group consisting of hydroxyapatite, polylactic acid, and polylactic glycolic acid.

7. The sheath of claim 1, wherein the first mesh tube and the second mesh tube are integrally formed.

8. The sheath of claim 1, further comprising a member coupling the first mesh tube with the second mesh tube.

9. The sheath of claim 8, wherein the member comprises a suture.

10. The sheath of claim 1, wherein the first mesh tube is smaller in diameter than the second mesh tube.

11. A soft tissue fixation assembly comprising a medical sheath and a fixation device, said medical sheath for organizing soft tissue and comprising:

a flexible mesh sleeve configured to be inserted into a bone tunnel;

a first mesh tube including a flexible body positioned within the mesh sleeve, wherein the first mesh tube is sized and shaped to conform to the shape of a shaft of said fixation device when the fixation device is received therein; and at least one second mesh tube substantially parallel and interconnected to the first tube and positioned within the sleeve, wherein the first mesh tube and the at least one second mesh tube are coupled together substantially along their lengths.

12. The sheath of claim 11, wherein the sleeve is sized and shaped to conform to the shaft of the fixation device when the fixation device is received within the first mesh tube.

* * * * *